United States Patent
Chaudhary et al.

(10) Patent No.: US 11,101,019 B2
(45) Date of Patent: Aug. 24, 2021

(54) METHODS FOR DETECTING MUTATION LOAD FROM A TUMOR SAMPLE

(71) Applicant: LIFE TECHNOLOGIES CORPORATION, Carlsbad, CA (US)

(72) Inventors: Ruchi Chaudhary, Redwood City, CA (US); Fiona Hyland, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 899 days.

(21) Appl. No.: 15/834,520

(22) Filed: Dec. 7, 2017

(65) Prior Publication Data

US 2018/0165410 A1 Jun. 14, 2018

Related U.S. Application Data

(60) Provisional application No. 62/431,493, filed on Dec. 8, 2016, provisional application No. 62/579,645, filed on Oct. 31, 2017, provisional application No. 62/585,598, filed on Nov. 14, 2017.

(51) Int. Cl.
*G16B 20/00* (2019.01)
*G16B 30/00* (2019.01)

(52) U.S. Cl.
CPC ............ *G16B 20/00* (2019.02); *G16B 30/00* (2019.02)

(58) Field of Classification Search
CPC ................................ G16B 20/00; G16B 30/00
USPC ........................................................ 702/19
See application file for complete search history.

(56) References Cited

U.S. PATENT DOCUMENTS

| | | |
|---|---|---|
| 2014/0336996 A1 | 11/2014 | Sun et al. |
| 2017/0213008 A1 | 7/2017 | Venn |

FOREIGN PATENT DOCUMENTS

| | | |
|---|---|---|
| WO | WO-2018106884 A1 | 6/2018 |

OTHER PUBLICATIONS

Alexandrov LB et al., "Mutational Signatures Associated with Tobacco Smoking In Human Cancer", Science, 2016, vol. 354, No. 6312, pp. 618-622.

Alexandrov LB et al., "Signatures of Mutational Processes in Human Cancer", Nature, 2013, vol. 500, pp. 415-421.

Hayward NK et al., "Whole-Genome Landscapes of Major Melanoma Subtypes", Nature, 2017, vol. 545, pp. 175-180.

PCT/US2019/048085, Search Report and Written Opinion, dated Dec. 2, 2019.

Rizvi et al., "Mutational landscape determines sensitivity to PD-1 blockade in non-small cell lung cancer", Science, 2016, vol. 348, pp. 124-128.

Snyder et al., "Genetic Basis for Clinical Response to CTLA-4 Blockade in Melanoma", N Engl J Med, 2014, vol. 371, pp. 2189-2199.

Van Allen et al., "Genomic correlates of response to CTLA-4 blockade in metastatic melanoma", Science, 2015, vol. 350, No. 6257, pp. 207-211.

Wong SQ et al., "Sequence Artefacts in A Prospective Series of Formalin-Fixed Tumours Tested for Mutations in Hotspot Regions by Massively Parallel Sequencing", BMC Medical Genomics, 2014, vol. 7, Article No. 23, 10 pages.

Campesato, L. et al., "Comprehensive cancer-gene panels can be used to estimate mutational load and predict clinical benefit to PD-1 blockade in clinical practice", *Oncotarget*, vol. 6, No. 33, Oct. 1, 2015, 34221-34227.

PCT/US2017/065053, International Search Report and Written Opinion dated Mar. 22, 2018, 14 pp.

Roszik, J. et al., "Novel algorithmic approach predicts tumor mutation load and correlates with immunotherapy clinical outcomes using a defined gene mutation set", *BMC Medicine*, vol. 14, No. 1; DOI: 10.1186/s12916-016-0705-4, Oct. 25, 2016, 8 pp.

Spranger, S. et al., "Density of immunogenic antigens does not explain the presence or absence of the T-cell-inflamed tumor microenvironment in melanoma", *Proceedings National Academy of Sciences (PNAS)*, vol. 113, No. 48; DOI: 10.1073/pnas. 1609376113, Nov. 11, 2016, E7759-E7768.

*Primary Examiner* — Jerry Lin
(74) *Attorney, Agent, or Firm* — Carolyn Koenig

(57) ABSTRACT

A targeted panel with low sample input requirements from a tumor only sample may be processed to estimate mutation load in a tumor sample. The method may include: detecting variants in nucleic acid sequence reads corresponding to targeted locations in the tumor sample genome; annotating detected variants with an annotation information from a population database; filtering the detected variants, wherein the filtering rule set retains the somatic variants and removes germ-line variants; counting the identified somatic variants to give a number of somatic variants; determining a number of bases in covered regions of the targeted locations in the tumor sample genome; and calculating a number of somatic variants per megabase, provides an estimate of the mutation load per megabase in the tumor sample genome.

20 Claims, 15 Drawing Sheets

METHODS FOR DETECTING MUTATION LOAD FROM A TUMOR SAMPLE

CROSS-REFERENCE

This application claims the benefit under 35 U.S.C. § 119(e) of U.S. Provisional Application No. 62/431,493, filed Dec. 8, 2016; U.S. Provisional Application No. 62/579,645, filed Oct. 31, 2017; and U.S. Provisional Application No. 62/585,598, filed Nov. 14, 2017. The entire contents of the aforementioned applications are incorporated by reference herein.

BRIEF SUMMARY OF THE INVENTION

High tumor mutation load is a biomarker that shown in some cancer types to predict positive response to immune checkpoint inhibitors. Current methods to estimate tumor mutation load may require large amounts of DNA to support whole exome sequencing and matched tumor and normal samples. A targeted panel with low sample input requirements from a tumor sample may be used to estimate mutation load in a tumor sample genome.

According to an exemplary embodiment, there is provided a method of analyzing a tumor sample genome for a mutation load, including the following steps: (1) detecting variants in a plurality of nucleic acid sequence reads to produce a plurality of detected variants, wherein the nucleic acid sequence reads correspond to a plurality of targeted locations in the tumor sample genome, wherein the detected variants include somatic variants and germ-line variants; (2) annotating one or more detected variants of the plurality of detected variants with an annotation information from one or more population databases, wherein the population databases include information associated with variants in a population, wherein the annotation information includes a minor allele frequency associated with a given variant; (3) filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants; (4) counting the identified somatic variants to give a number of somatic variants; (5) determining a number of bases in covered regions of the targeted locations in the tumor sample genome; and (6) calculating a number of somatic variants per megabase by dividing the number of identified somatic variants by the number of bases in the covered regions to produce the mutation load for the tumor sample genome.

According to an exemplary embodiment, there is provided a system for analyzing a tumor sample genome for a mutation load, comprising a processor and a data store communicatively connected with the processor, the processor configured to perform the steps including: detecting variants in a plurality of nucleic acid sequence reads to produce a plurality of detected variants, wherein the nucleic acid sequence reads correspond to a plurality of targeted locations in the tumor sample genome, wherein the detected variants include somatic variants and germ-line variants; annotating one or more detected variants of the plurality of detected variants with an annotation information from one or more population databases stored in the data store, wherein the population databases include information associated with variants in a population, wherein the annotation information includes a minor allele frequency associated with a given variant; filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants; counting the identified somatic variants to give a number of somatic variants; determining a number of bases in covered regions of the targeted locations in the tumor sample genome; and calculating a number of somatic variants per megabase by dividing the number of identified somatic variants by the number of bases in the covered regions to produce the mutation load for the tumor sample genome.

According to an exemplary embodiment, there is provided a non-transitory machine-readable storage medium comprising instructions which, when executed by a processor, cause the processor to perform a method for analyzing a tumor sample genome for a mutation load, including: (1) detecting variants in a plurality of nucleic acid sequence reads to produce a plurality of detected variants, wherein the nucleic acid sequence reads correspond to a plurality of targeted locations in the tumor sample genome, wherein the detected variants include somatic variants and germ-line variants; (2) annotating one or more detected variants of the plurality of detected variants with an annotation information from one or more population databases, wherein the population databases include information associated with variants in a population, wherein the annotation information includes a minor allele frequency associated with a given variant; (3) filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants; (4) counting the identified somatic variants to give a number of somatic variants; (5) determining a number of bases in covered regions of the targeted locations in the tumor sample genome; and (6) calculating a number of somatic variants per megabase by dividing the number of identified somatic variants by the number of bases in the covered regions to produce the mutation load for the tumor sample genome.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
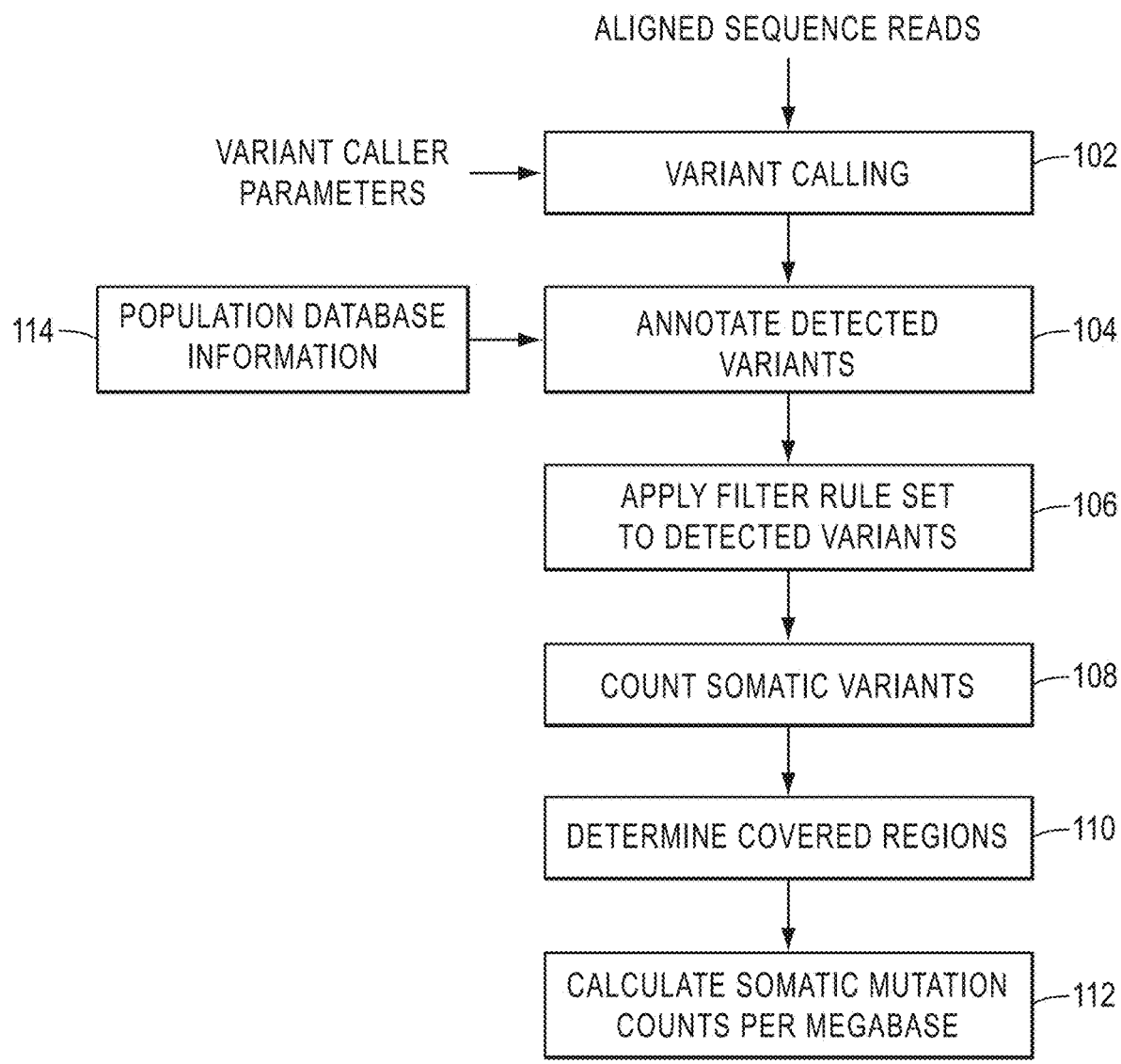
FIG. 1 is a block diagram of a method of detecting tumor mutation load, according to an exemplary embodiment.

In accordance with the teachings and principles embodied in this application, new methods, systems and non-transitory machine-readable storage medium are provided to estimate tumor mutation load by analysis of nucleic acid sequence reads from a tumor only sample genome.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," "nucleic acid sequence read" or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

The phrase "base space" refers to a nucleic acid sequence data schema where nucleic acid sequence information is represented by the actual nucleotide base composition of the nucleic acid sequence. For example, the nucleic acid sequence "ATCGA" is represented in base space by the actual nucleotide base identities (for example, A, T/or U, C, G) of the nucleic acid sequence.

The phrase "flow space" refers to a nucleic acid sequence data schema wherein nucleic acid sequence information is represented by nucleotide base identifications (or identifications of known nucleotide base flows) coupled with signal or numerical quantification components representative of nucleotide incorporation events for the nucleic acid sequence. The quantification components may be related to the relative number of continuous base repeats, such as homopolymers, whose incorporation is associated with a respective nucleotide base flow. For example, the nucleic acid sequence "ATTTGA" may be represented by the nucleotide base identifications A, T, G and A (based on the nucleotide base flow order) plus a quantification component for the various flows indicating base presence/absence as well as possible existence of homopolymers. Thus for "T" in the example sequence above, the quantification component may correspond to a signal or numerical identifier of greater magnitude than would be expected for a single "T" and may be resolved to indicate the presence of a homopolymer stretch of "T"s (in this case a 3-mer) in the "ATTTGA" nucleic acid sequence.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, for example 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The phrase "genomic variants" or "genome variants" denote a single or a grouping of sequences (in DNA or RNA) that have undergone changes as referenced against a particular species or sub-populations within a particular species due to mutations, recombination/crossover or genetic drift. Examples of types of genomic variants include, but are not limited to: single nucleotide polymorphisms (SNPs), copy number variations (CNVs), insertions/deletions (Indels), inversions, etc.

In various embodiments, genomic variants can be detected using a nucleic acid sequencing system and/or analysis of sequencing data. The sequencing workflow can begin with the test sample being sheared or digested into hundreds, thousands or millions of smaller fragments which are sequenced on a nucleic acid sequencer to provide hundreds, thousands or millions of sequence reads, such as nucleic acid sequence reads. Each read can then be mapped to a reference or target genome, and in the case of mate-pair fragments, the reads can be paired thereby allowing interrogation of repetitive regions of the genome. The results of mapping and pairing can be used as input for various standalone or integrated genome variant (for example, SNP, CNV, Indel, inversion, etc.) analysis tools.

The phrase "sample genome" can denote a whole or partial genome of an organism.

The term "allele" as used herein refers to a genetic variation associated with a gene or a segment of DNA, i.e., one of two or more alternate forms of a DNA sequence occupying the same locus.

The term "locus" as used herein refers to a specific position on a chromosome or a nucleic acid molecule. Alleles of a locus are located at identical sites on homologous chromosomes.

As used herein, a "targeted panel" refers to a set of target-specific primers that are designed for selective amplification of target gene sequences in a sample. In some embodiments, following selective amplification of at least one target sequence, the workflow further includes nucleic acid sequencing of the amplified target sequence.

As used herein, "target sequence" or "target gene sequence" and its derivatives, refers to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As used herein, "target-specific primer" and its derivatives, refers to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence.

Tumor mutation load (TML) is a measure of the number of mutations within a tumor genome, defined as the total number of mutations per coding area of a tumor genome. Recent studies have shown tumor mutation load to be a sensitive marker that can help predict responses to certain cancer immunotherapies. Immunotherapies have shown anti-cancer effects in melanoma, non-small-cell lung carcinoma (NSCLC), and bladder cancer, among other cancers. High tumor mutation load is associated with positive responses from immune checkpoint inhibitors. Hence high mutation load of a tumor may act as a predictive biomarker for immunotherapy. However, existing methods to estimate tumor mutation load have large input DNA and extensive infrastructure requirements and are associated with delays due to shipping precious biopsy samples to central laboratories.

In some embodiments, a targeted panel with low sample input requirements may be used to estimate mutation load in a tumor sample. A targeted panel for tumor mutation load, or TML panel, provides a viable alternative to whole exome sequencing (WES). In some embodiments, the targeted panel may comprise the Comprehensive Cancer Panel (CCP) available from Thermo Fisher Scientific (SKU 4477685). The CCP interrogates 409 cancer genes, such as oncogenes and tumor suppressor genes, using highly multiplexed amplification with 4 pools of primer pairs that are targeted to the panel genes. In some embodiments, the CCP may be modified to function with two combined pools instead of four pools to reduce DNA sample size. Removing the overlapping primers in the combined pools may reduce number of primers in the modified CCP panel to produce a targeted panel for TML including the same genes as the CCP. The targeted panel interrogates 409 key cancer genes covering approximately 1.7 megabases (Mb) of genomic space. In some embodiments, the workflow may require up to 20 ng DNA from formalin-fixed paraffin-embedded (FFPE) or other sample types. In other embodiments, the workflow may use about 1 ng to about 40 ng sample DNA. In other embodiments, the workflow may use about 1 ng to about 20 ng or about 10 ng to about 20 ng sample DNA. The embodiments described herein do not require analysis of a matched normal sample to estimate the tumor mutation load.

In some embodiments, the panel may comprise the Oncomine Comprehensive Assay v3 (OCAv3) available from Thermo Fisher Scientific (SKU A35806 or SKU A36111). The OCAv3 panel interrogates 161 cancer-related genes and enables detection of SNVs (single nucleotide variants), CNVs (copy number variants), gene fusions and indels using primer pairs targeted to the genes of the panel. In some embodiments, the panel may comprise a custom panel or other targeted panel of cancer driver or other genes associated with cancer.

FIG. 1 is a block diagram of a method of detecting tumor mutation load, according to an exemplary embodiment. In the variant calling step 102, a processor receives aligned sequence reads resulting from targeted sequencing of a tumor sample. The aligned sequence reads can be retrieved from a file using a BAM file format, for example. The aligned sequence reads may correspond to a plurality of targeted locations in the tumor sample genome. The variant calling step 102 may be configured by one or more variant caller parameters. In some embodiments, variant caller parameters may include parameters for minimum allele frequency, strand bias and data quality stringency. The minimum allele frequency parameter sets the minimum observed allele frequency required for a non-reference variant call. The strand bias indicates a relative proportion of variant reads in forward and reverse directional sequencing. The strand bias parameter sets a maximum level for strand bias such that a variant is not called if the proportion of variant reads observed in one of the directional sequencings exceeds the strand bias parameter. The data quality stringency parameter sets a threshold for read quality required to make a variant call. In some embodiments, the variant caller parameters for single nucleotide variant (SNV) detection may be set to the values given in Table 1.

TABLE 1

| Variant Caller Parameter | Value | Range |
| --- | --- | --- |
| Minimum Allele Frequency | 0.05 or 0.1 | 0.001 to 0.15 |
| Strand Bias | 0.9 | 0.54 to 0.95 |
| Data Quality Stringency | 20 | 5 to 25 |

In some embodiments, variant caller parameters may include a minimum coverage parameter, or minimum read depth parameter, that sets a minimum coverage required for a variant to be called. The minimum coverage parameter may be set to levels to reduce C>T or G>A type nonsystematic noise. The minimum coverage parameter may be set in a range from 20 to 60. The minimum coverage parameter of 20 gives a 10% level of detection (LOD) and minimum coverage parameter of 60 gives a 5% level of LOD.

Figure 15:
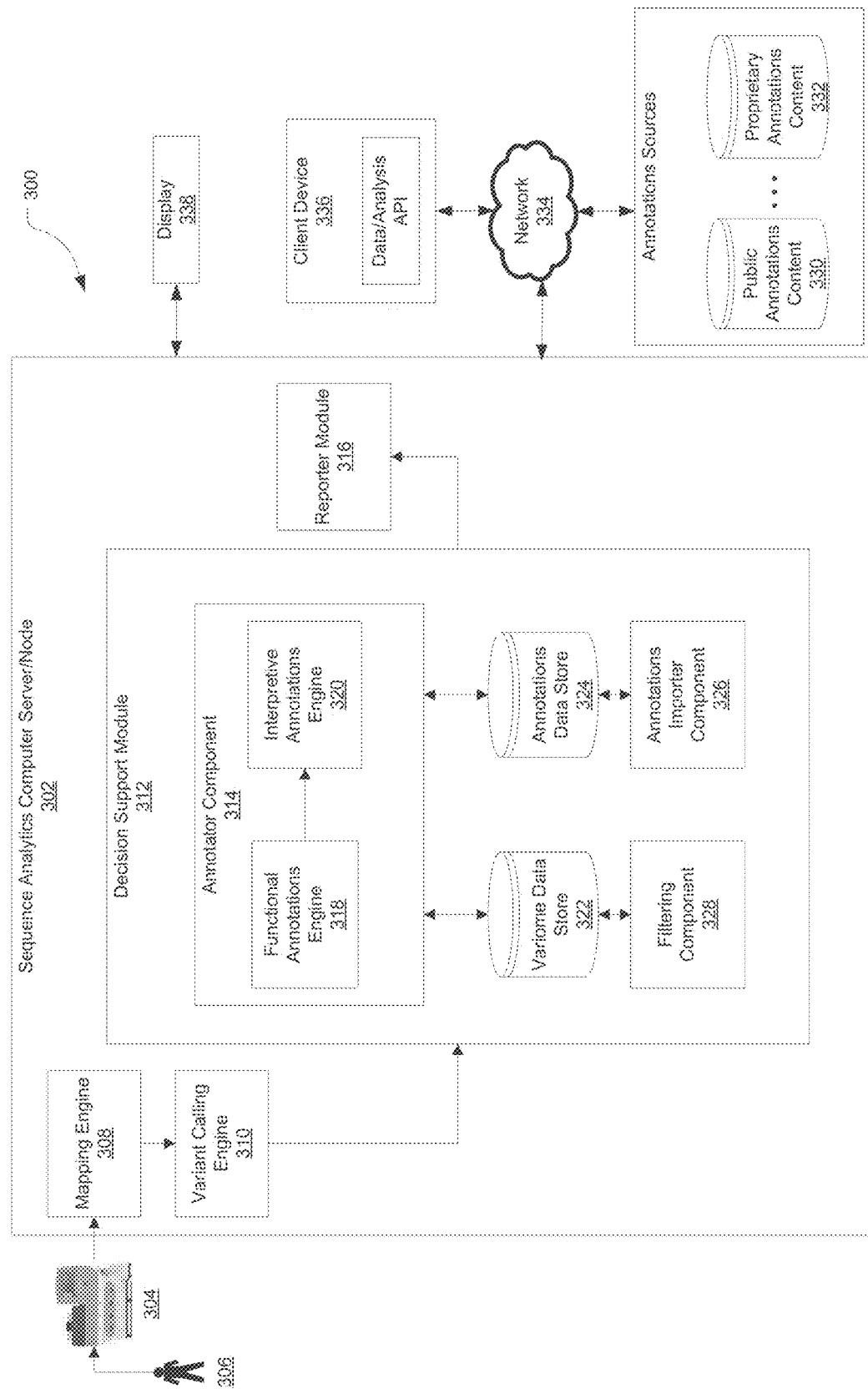
FIG. 15 is a schematic diagram of a system for annotating genomic variants, in accordance with various embodiments.

In some embodiments the aligned sequence reads are provided by the mapping engine 308 described with respect to FIG. 15. In some embodiments the variant calling step 102 may be implemented by the variant calling engine 310 described with respect to FIG. 15. In some embodiments, the variant detection methods for use with the present teachings may include one or more features described in U.S. Pat. Appl. Publ. No. 2013/0345066, published Dec. 26, 2013, U.S. Pat. Appl. Publ. No. 2014/0296080, published Oct. 2, 2014, and U.S. Pat. Appl. Publ. No. 2014/0052381, published Feb. 20, 2014, each of which incorporated by reference herein in its entirety. In some embodiments, other variant detection methods may be used. In various embodiments, a variant caller can be configured to communicate variants called for a sample genome as a *.vcf, *.gff, or *.hdf data file. The called variant information can be communicated using any file format as long as the called variant information can be parsed and/or extracted for analysis.

Returning to FIG. 1, in the variant annotating step 104, a processor annotates the detected variants with information associated with the respective variants from one or more population databases. In some embodiments, the annotation information may include the minor allele frequency (MAF) of the variant. The population database may provide public annotation information content or proprietary annotation information content. For example, publicly available population databases include: 5000 exomes—NHLBI Exome Sequencing Project (http://evs.gs.washington.edu/EVS/), 1000 genomes—International Genome Sample Resource (IGSR) (http://www.internationalgenome.org/home) and ExAC—Exome Aggregation Consortium (http://exac.broadinstitute.org) and UCSC common SNPs (https://genome.ucsc.edu/). Annotation information from other population databases in addition to or in place of these databases may be used. It may be understood that as genetic information resources develop new and more extensive databases may become available.

In some embodiments the annotating step 106 may be implemented in the annotator component 314 and the population database information may be stored in annotations data store 324 described with respect to FIG. 15. In some embodiments, the annotation methods for use with the present teachings may include one or more features described in U.S. Pat. Appl. Publ. No. 2016/0026753, published Jan. 28, 2016, incorporated by reference herein in its entirety.

In the filtering step 106, the processor applies a rule set to retain somatic variants and remove germ-line variants from the detected variants. In some embodiments, a filter rule set is applied to each detected variant and includes at least some of the rules listed in Table 2.

TABLE 2

| | Filter Rule |
| --- | --- |
| 1. | Retain SNVs; optionally filter out other variant types, such as indels and MNVs |
| 2. | Filter out SNVs inside homopolymers with lengths greater than 7. |
| 3. | Retain variants found in 1000 genomes with MAF in a given MAF range; filter out variants outside the MAF range. |
| 4. | Retain variants found in 5000 exomes with MAF in a given MAF range; filter out variants outside the MAF range. |
| 5. | Retain variants found in ExAC with MAF in a given MAF range; filter out variants outside the MAF range. |
| 6. | Filter out variants found in UCSC common SNPs. |

In some embodiments, a particular type of variant is retained, such as SNVs only, for further analysis while other types of variants are filtered out. Optionally, other types of variants, such as indels, may be retained for further analysis. In some embodiments, variants in regions with homopolymer lengths greater than 7 are filtered out to mitigate lower accuracy in base calling for long homopolymers. In filter rules 3, 4 and 5, detected variants are retained if the MAF indicated by the population database is within a given MAF range. The MAF is included in the annotation information associated with the detected variants by the annotating step 104. In a preferred embodiment, the MAF range is [0 $10^{-6}$], or MAF is less than or equal to $10^{-6}$. In some embodiments, the MAF range may be [0 0.001], [0 0.002] or [0 0.01]. The MAF ranges may be the same or different for the population databases, such as the 1000 genomes, 5000 exomes and ExAC databases. In filter rule 6, variants found in the UCSC common SNPs database are filtered out. The filter rule set applied to the detected variants removes the germ-line variants and retains the somatic variants to produce identified somatic variants.

In the counting step 108, the processor counts the identified somatic variants to produce a somatic mutation count. In the determining step 110, the processor determines the covered regions of the aligned sequence reads where the coverage of a given base position is at least a threshold coverage. In some embodiments, the threshold coverage may be in a range of 20 to 60 sequence reads. The threshold coverage of 20 corresponds to a workflow for a 10% LOD. The threshold coverage of 60 corresponds to a workflow for a 5% LOD. The processor counts the number of bases in the covered regions to produce the covered base count in megabases (Mb). In the calculating step 112, the processor divides the somatic mutation count by the covered base count to form an estimate of the tumor mutation load in number of somatic mutations per Mb for the tumor sample genome. The tumor mutation load estimate may be provided in a report to the user.

Figure 2A:
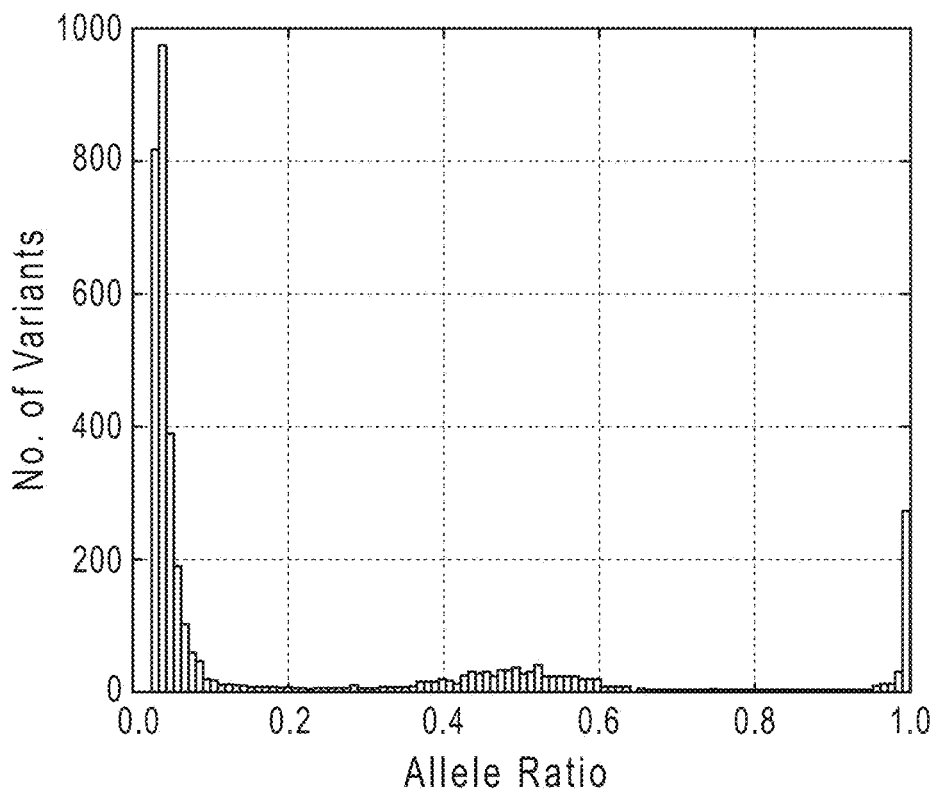
FIG. 2A is an example of a histogram plot of the number of variants per allele ratio including all detected variants, both germ-line and somatic variants.
Figure 2B:
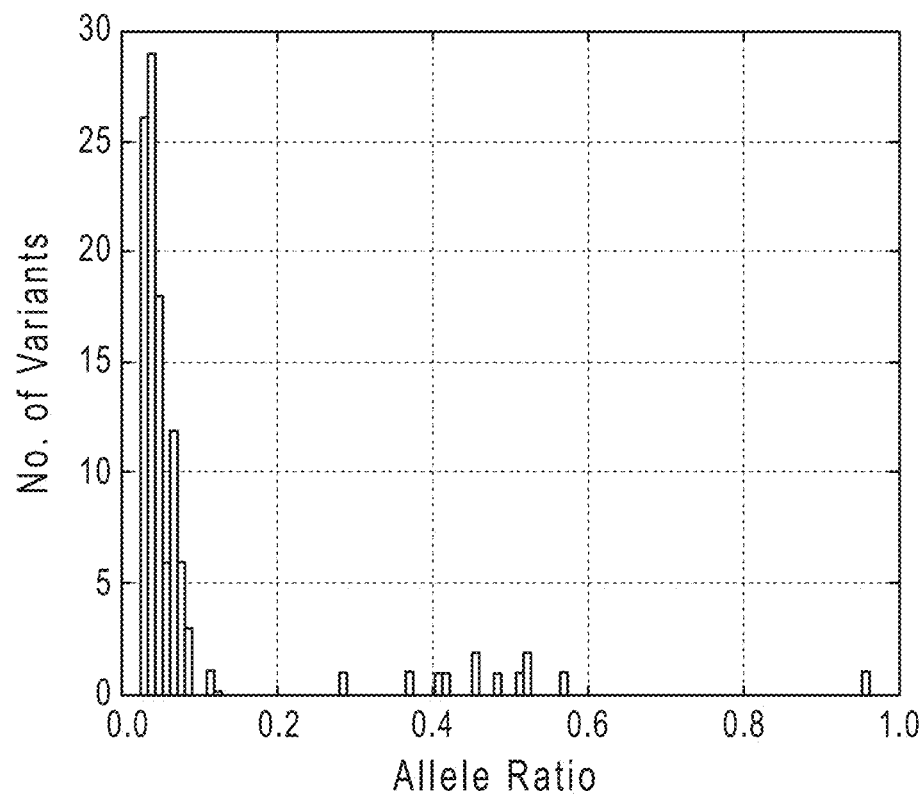
FIG. 2B is an example of a histogram plot of the number of variants per allele ratio after applying the filter rule set to remove the germ-line variants.
Figure 3A:
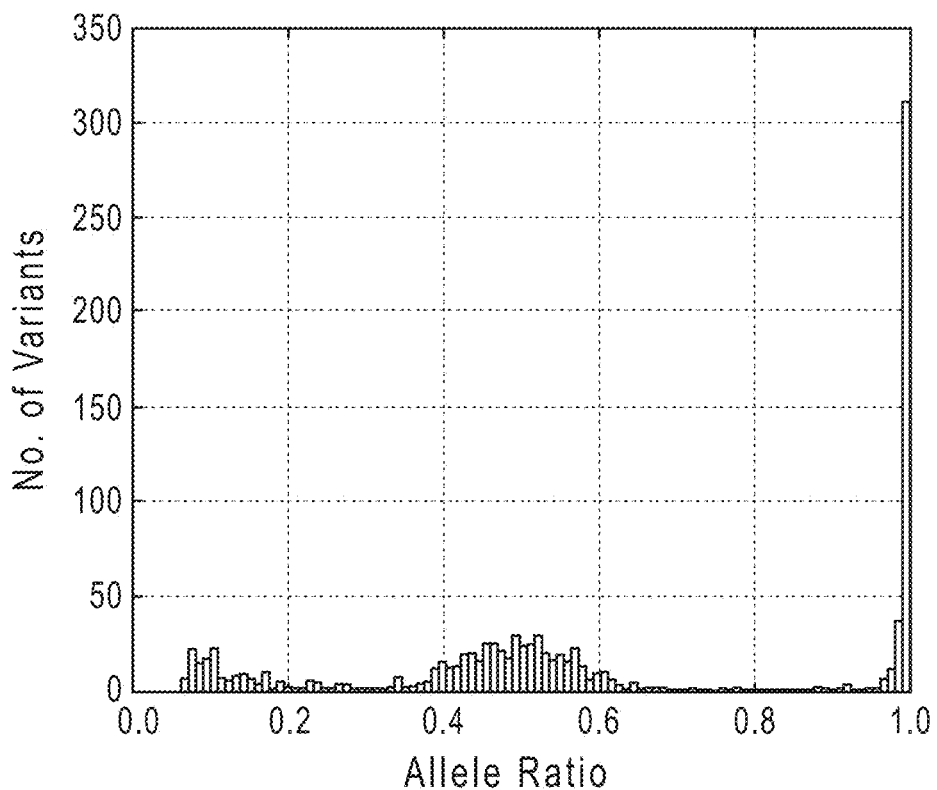
FIG. 3A is an example of a histogram plot of the number of variants per allele ratio including all detected variants, both germ-line and somatic variants.
Figure 3B:
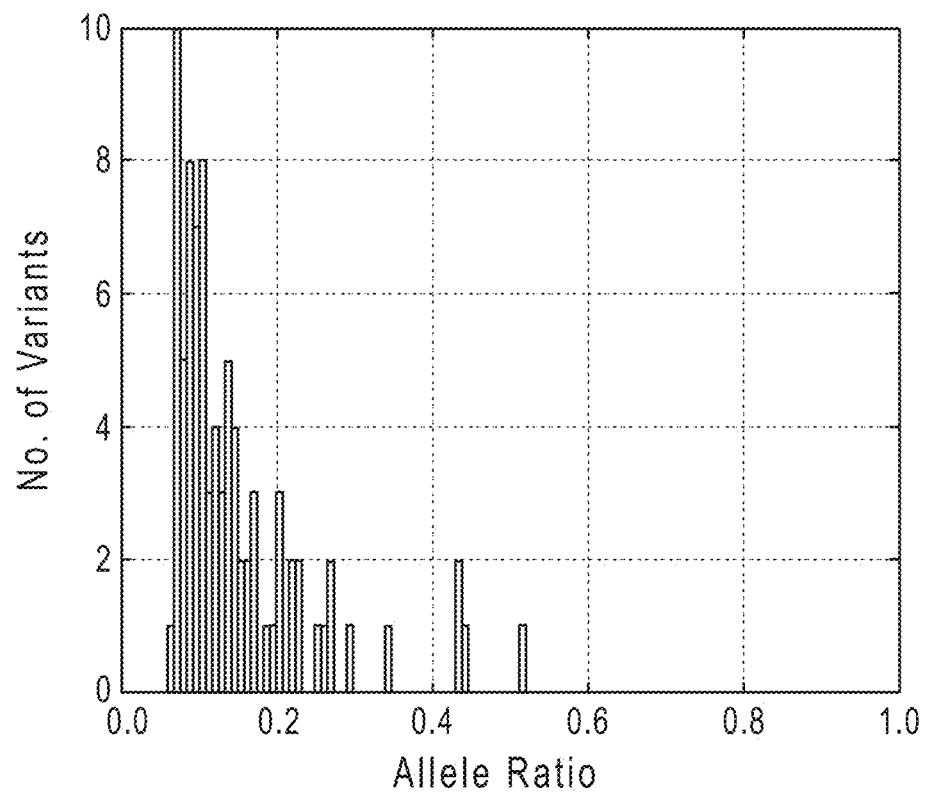
FIG. 3B is an example of a histogram plot of the number of variants per allele ratio after applying the filter rule set to remove the germ-line variants.
Figure 4A:
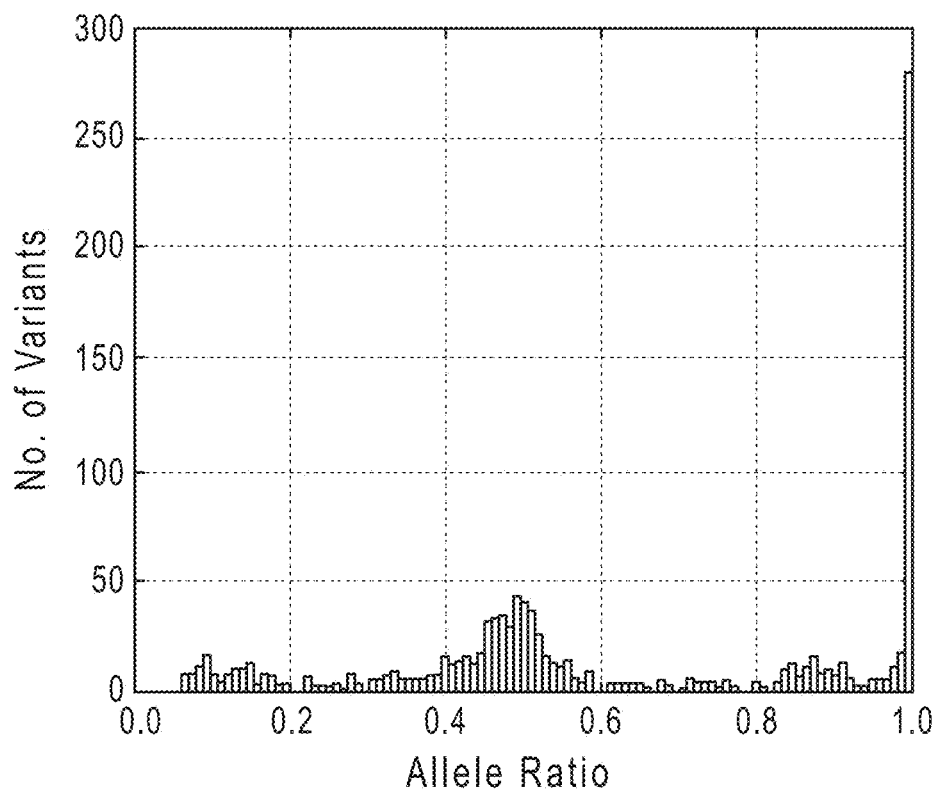
FIG. 4A is an example of a histogram plot of the number of variants per allele ratio including all detected variants, both germ-line and somatic variants.
Figure 4B:
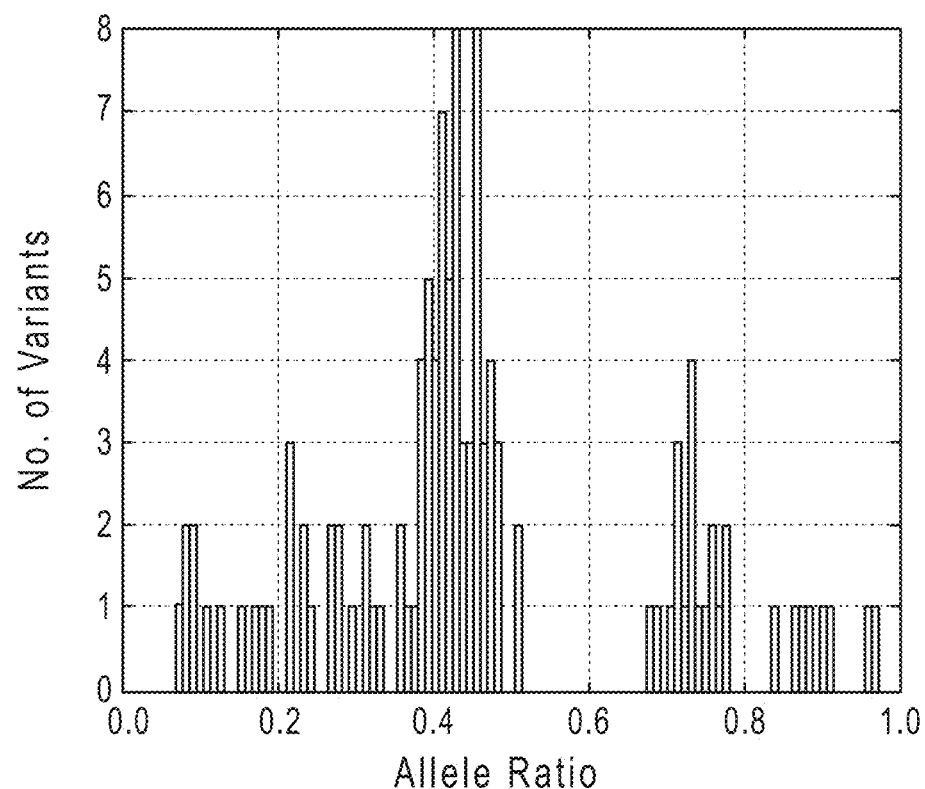
FIG. 4B is an example of a histogram plot of the number of variants per allele ratio after applying the filter rule set to remove the germ-line variants.

FIGS. 2A-2B, 3A-3B and 4A-4B show examples of results before and after applying the filter rule set 106 described with respect to FIG. 1. FIGS. 2A, 3A are 4A show histogram plots of the number of variants per allele ratio including all detected variants, both germ-line and somatic variants. The allele ratio of an allele is the ratio of number of reads supporting this allele to the total number of reads at the respective position. A cluster of detected variants near an allele ratio of 0.5 may indicate germ-line alleles from one parent. A cluster of detected variants near an allele ratio of 1.0 may indicate germ-line alleles from both parents. FIGS. 2B, 3B are 4B show histogram plots of the number of variants per allele ratio after applying the filter rule set to remove the germ-line variants by the filtering step 106. Numbers of variants are significantly reduced, as shown in FIGS. 2B, 3B and 4B and in Table 3. Table 3 also gives the results on somatic mutations per megabase, or mutation load per megabase.

TABLE 3

| FIG. NO. | NO. OF VARIANTS BEFORE FILTER 106 | NO. OF VARIANTS AFTER FILTER 106 | SOMATIC MUTATIONS/MB |
|---|---|---|---|
| 2A (BEFORE); 2B (AFTER) | 3,706 | 113 | 52.24 |
| 3A (BEFORE); 3B (AFTER) | 1,057 | 120 | 73.14 |
| 4A (BEFORE); 4B (AFTER) | 1,111 | 113 | 68.84 |

Figure 5:
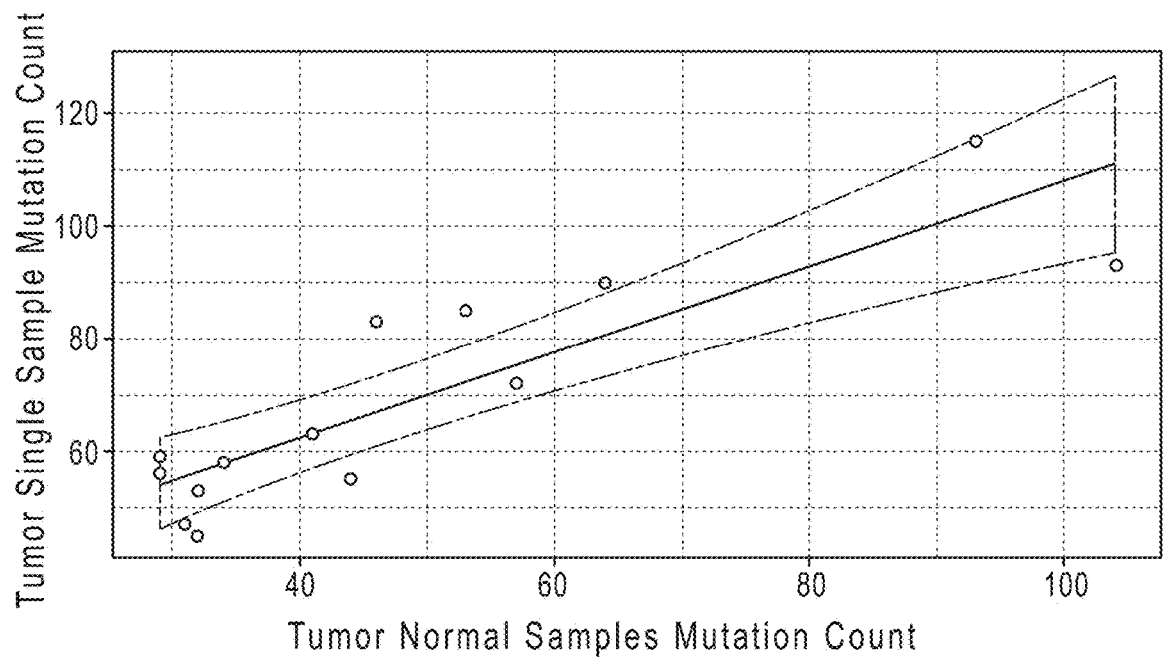
FIG. 5 shows an example of comparisons of somatic SNV mutation counts resulting from analysis of tumor sample only and analysis of matched tumor-normal samples.
Figure 6:
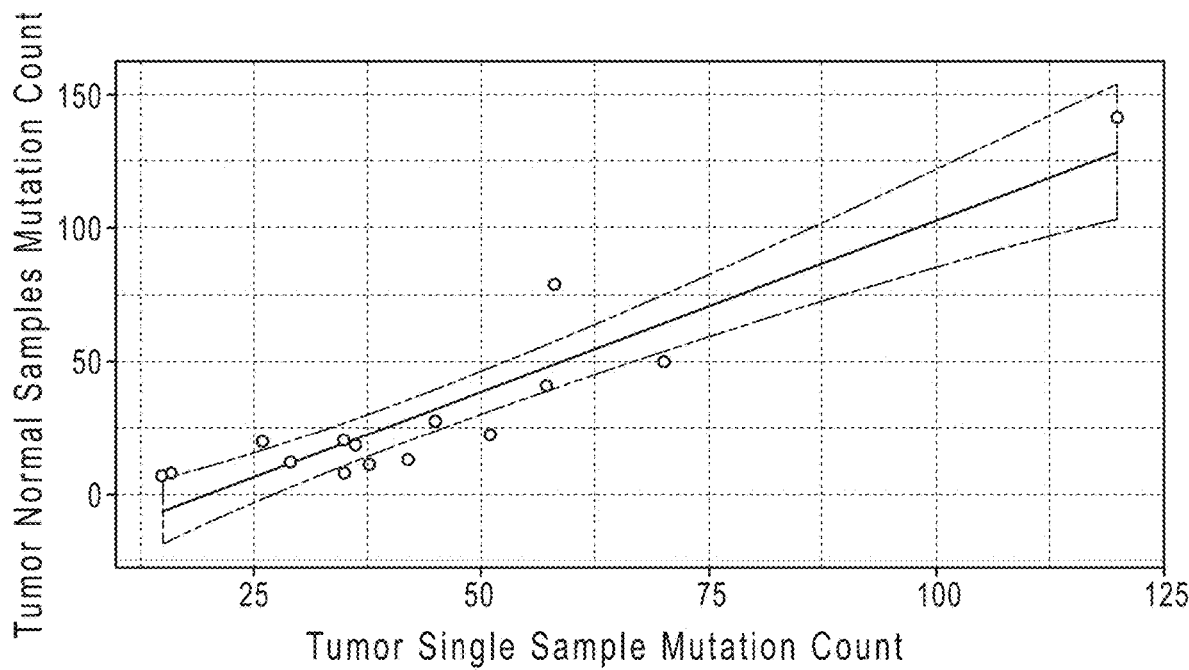
FIG. 6 shows an example of comparisons of somatic SNV mutation counts resulting from analysis of tumor sample only and analysis of matched tumor-normal samples.

To test the effectiveness of the tumor only analysis in counting somatic variants, mutation counts resulting from of tumor only analysis and matched tumor-normal analysis were compared. FIGS. 5 and 6 shows examples of comparisons of somatic SNV mutation counts resulting from analysis of tumor sample only and analysis of matched tumor-normal samples. The somatic mutation counts in FFPE tumor only samples determined using the method described with respect to FIG. 1 were highly concordant with somatic mutation counts determined by matched tumor-normal sequencing. Mutation counts from tumor only analysis strongly correlate with those of tumor-normal analysis. For the results of FIG. 5, the coefficient of determination, $r2=0.80$. For the results of FIG. 6, the correlation coefficient, $r=0.9233$.

Figure 7:
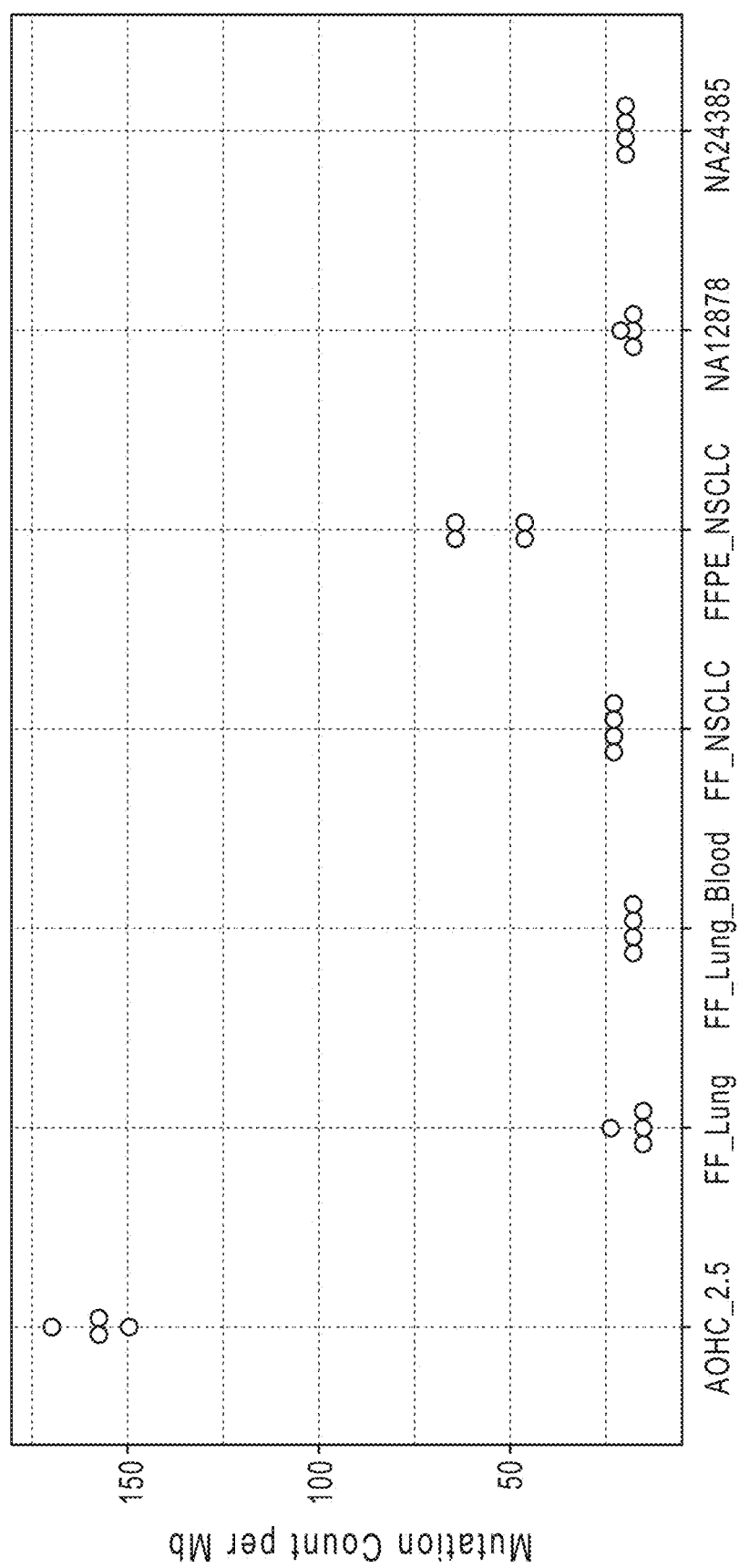
FIG. 7 shows the results of testing the reproducibility of the somatic mutation counts.

FIG. 7 shows the results of testing the reproducibility of the somatic mutation counts. The results show that the somatic mutation loads estimated using the method described with respect to FIG. 1 were highly reproducible. Sample types included cell lines, FFPE and fresh frozen (FF) lung samples.

Cell line samples were obtained from NIGMS Human Genetic Cell Repository at the Coriell Institute for Medical Research. FFPE and FF samples were obtained from Biochain, Bioreclamation and Conversant. Control samples were obtained from Acrometrix.

Figure 8:
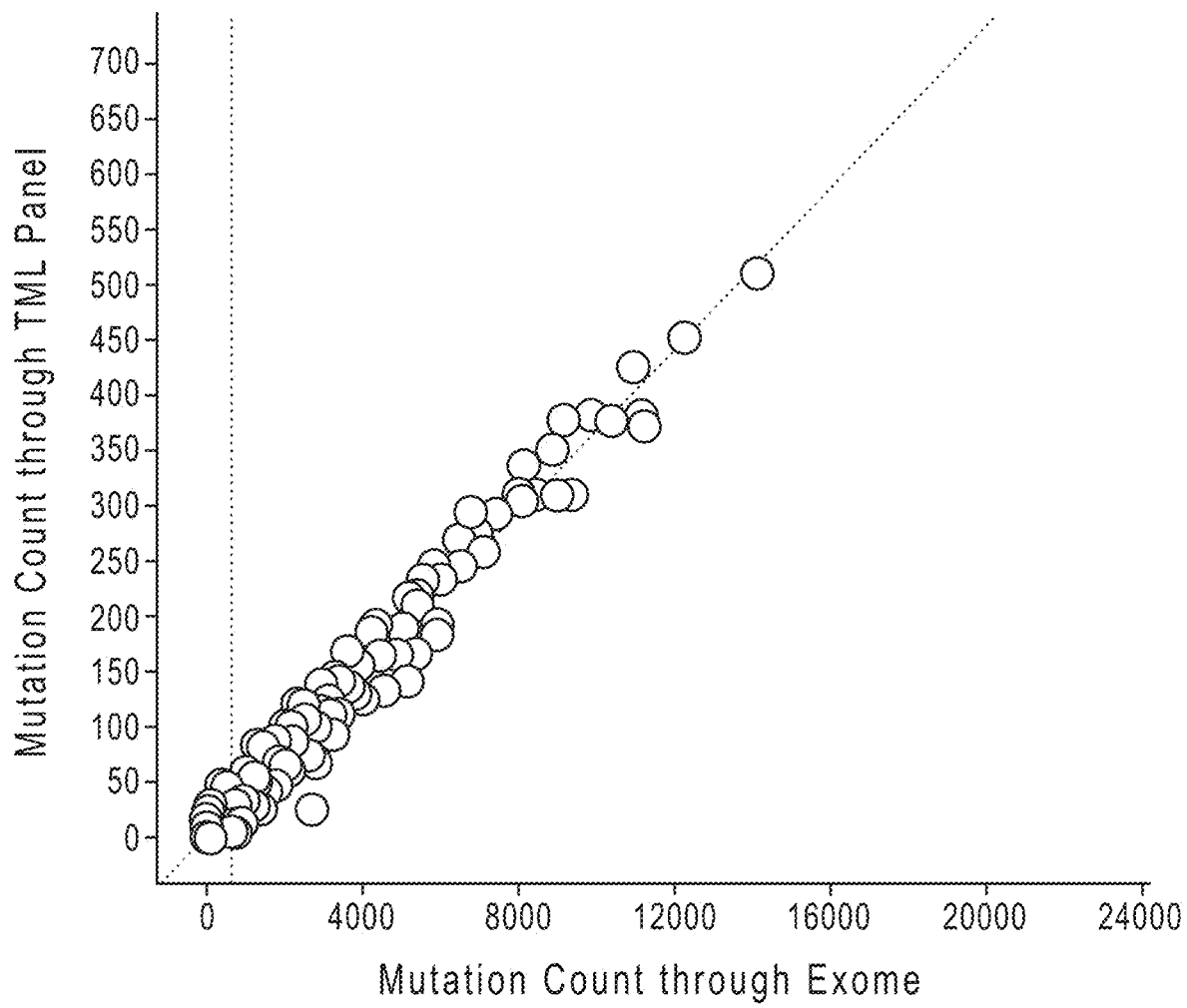
FIG. 8 shows a plot comparing the mutation count through the targeted panel for TML versus the mutation count through WES.

In silico analyses show that the targeted panel correlates well with whole exome sequencing results for mutation counts. A somatic variant dataset of WES data was derived from the COSMIC v80 database containing 21,056 exomes derived from 22 major cancer types (http://cancer.sanger.ac.uk/cosmic). Somatic mutations in the somatic variant dataset were restricted to those covered by the targeted panel for TML. FIG. 8 shows a plot comparing the mutation count through the targeted panel for TML versus the mutation count through WES. The mutation counts plotted represent cancer types, including bladder cancer, brain and central nervous system (CNS) cancer, breast cancer, cervical cancer, colorectal cancer, endometrial cancer, esophageal cancer, gastric cancer, head and neck cancer, kidney cancer, leukemia, liver cancer, lung cancer, lymphoma, melanoma, myeloma, other cancer, ovarian cancer, pancreatic cancer, prostate cancer, sarcoma and thyroid cancer. Somatic mutation counts in WES strongly correlated with mutation counts in the targeted panel for TML with $r2=0.968$.

Figure 9A:
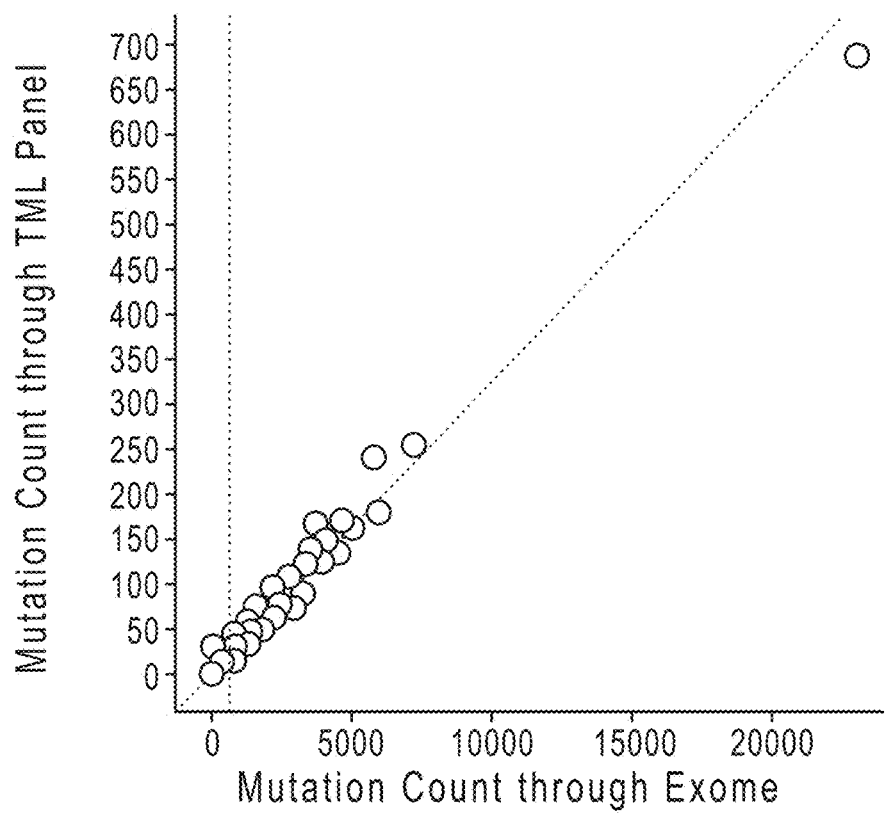
FIG. 9A shows the comparison of mutation counts between the targeted panel and WES for melanoma.
Figure 9B:
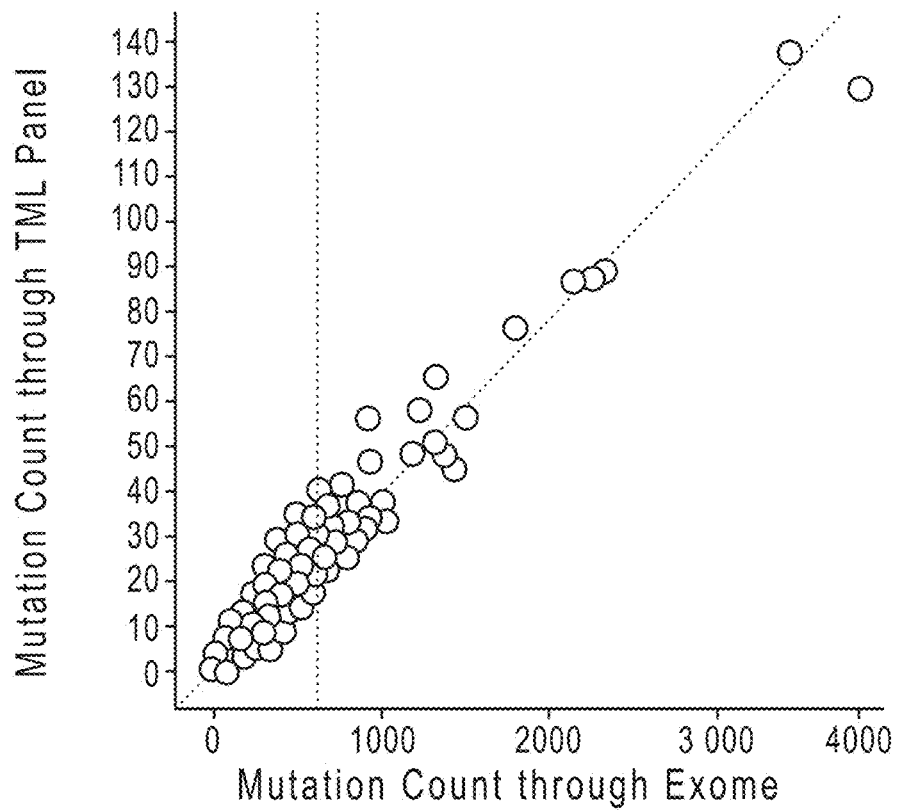
FIG. 9B shows the comparison of mutation counts between the targeted panel and WES for lung cancer.
Figure 9C:
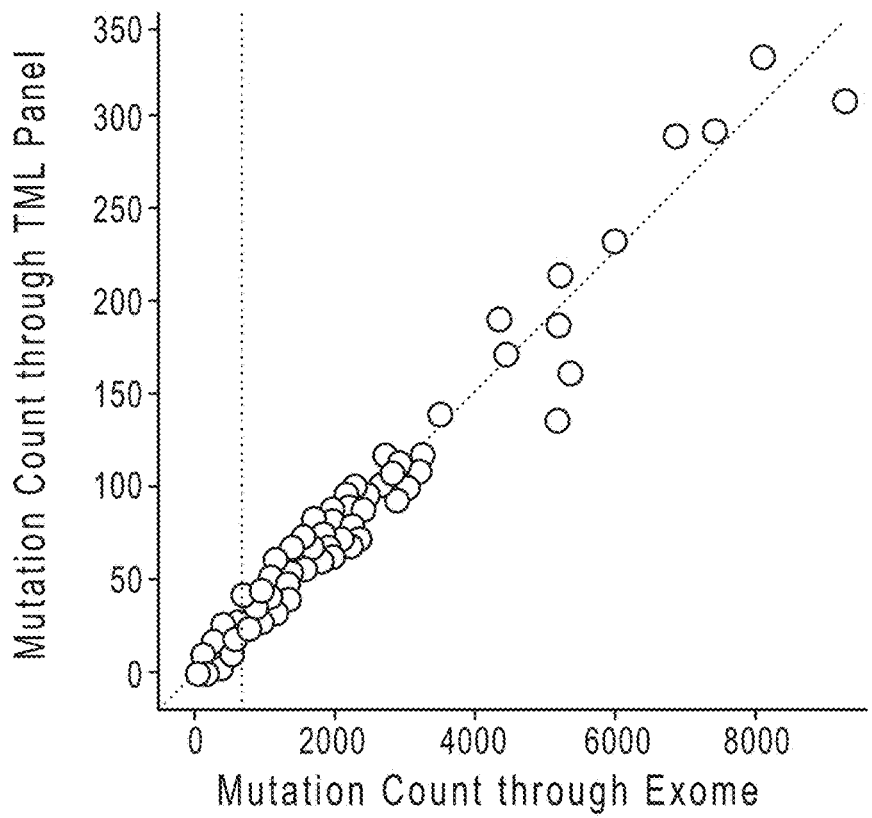
FIG. 9C shows the comparison of mutation counts between the targeted panel and WES for colorectal cancer.
Figure 9D:
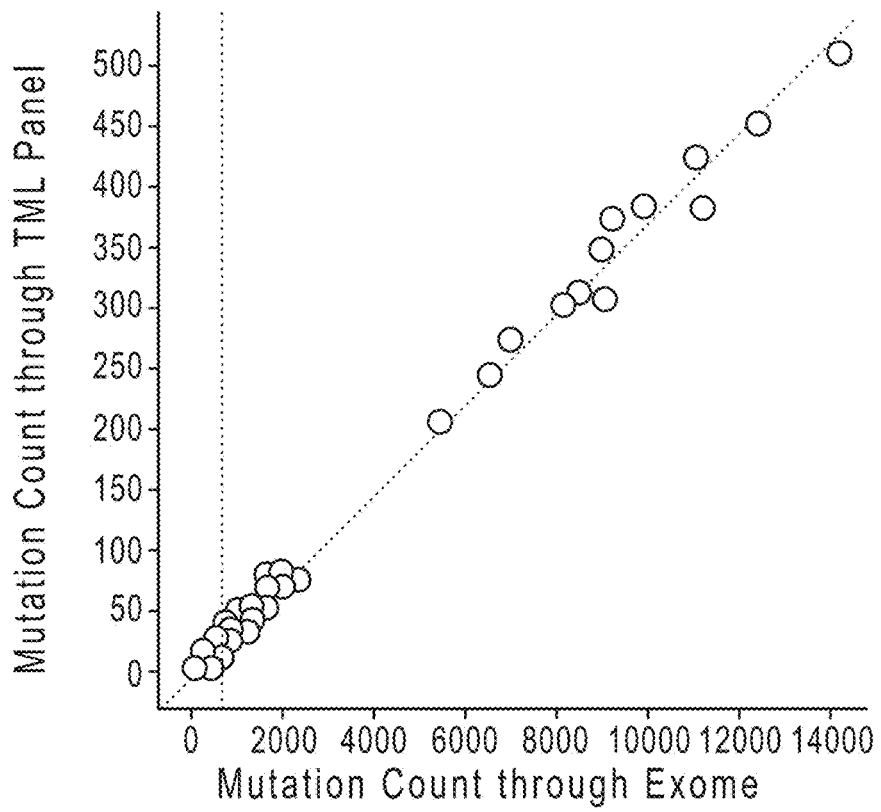
FIG. 9D shows the comparison of mutation counts between the targeted panel and WES for endometrial cancer.

FIGS. 9A-9D show plots comparing the mutation count through the targeted panel for TML versus the mutation count through WES for single cancer types extracted from FIG. 8. FIG. 9A shows the comparison of mutation counts between the targeted panel and WES for melanoma, where $r2=0.976$. FIG. 9B shows the comparison of mutation counts between the targeted panel and WES for lung cancer, where $r2=0.935$. FIG. 9C shows the comparison of mutation counts between the targeted panel and WES for colorectal cancer, where $r2=0.975$. FIG. 9D shows the comparison of mutation counts between the targeted panel and WES for endometrial cancer, where $r2=0.995$. The results described with respect to FIG. 8 and FIGS. 9A-9D show that the targeted panel is suitable for TML estimation.

Figure 10A:
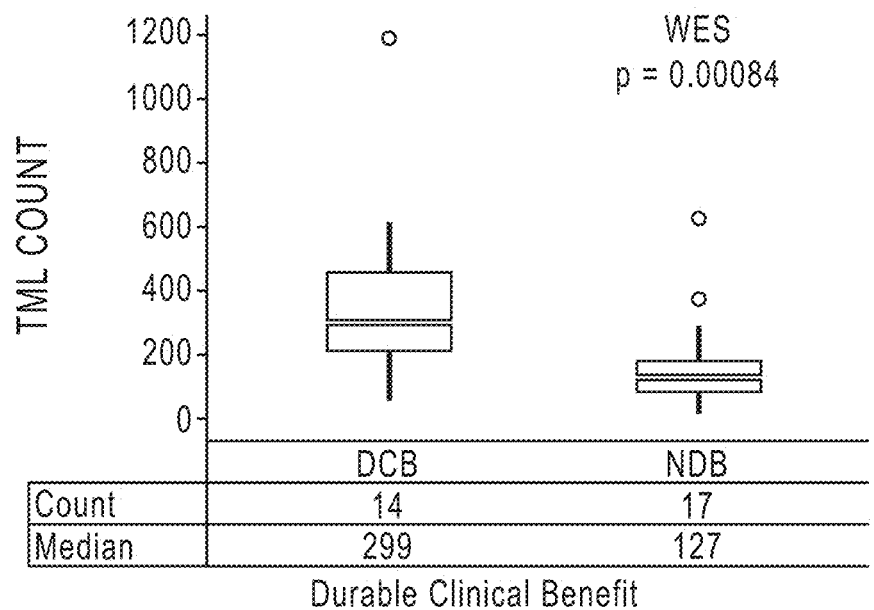
FIG. 10A shows an example of box plots for the WES TML counts versus clinical response.
Figure 10B:
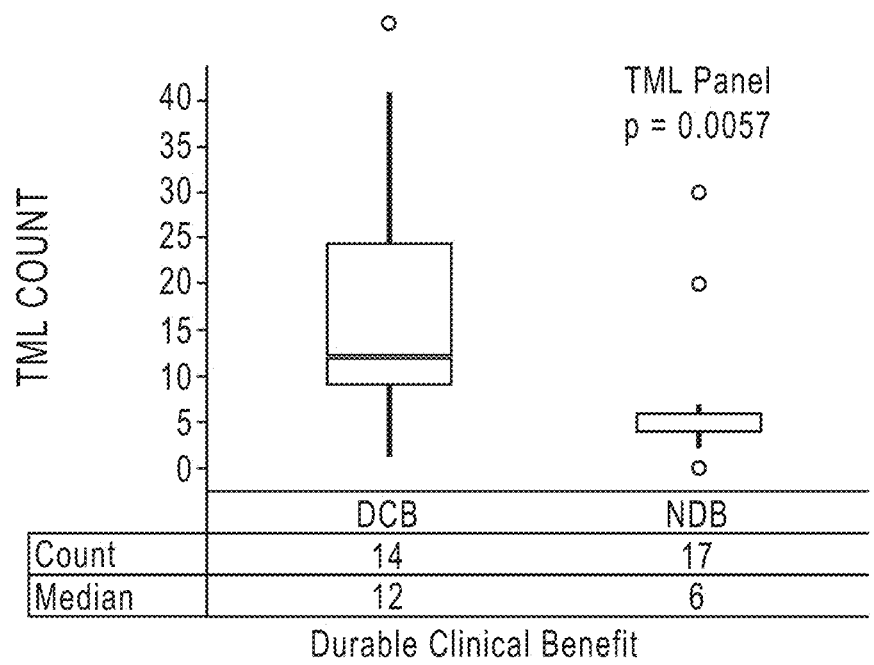
FIG. 10B shows an example of box plots for the somatic mutation counts intersecting with the targeted panel versus clinical response.
Figure 11A:
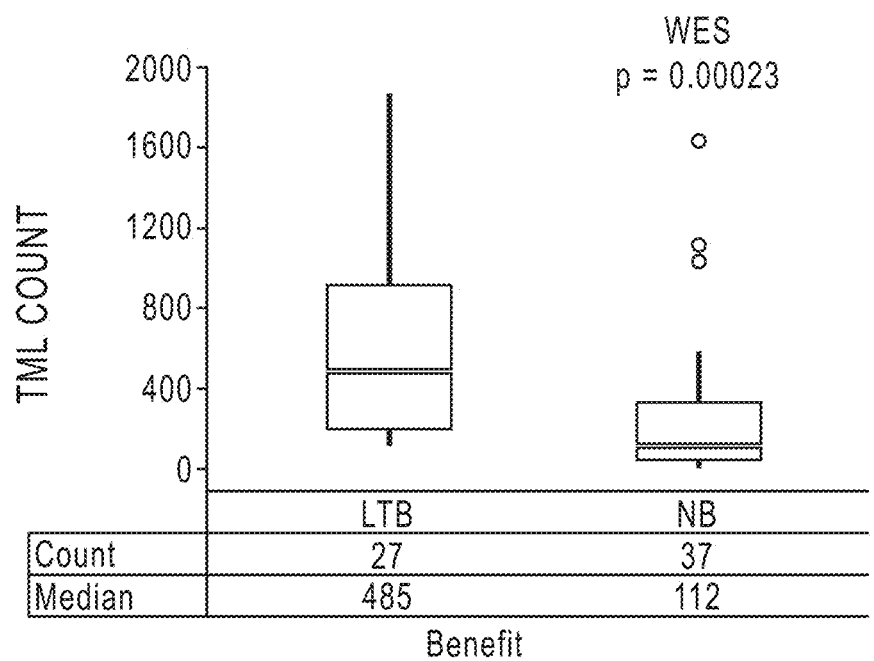
FIG. 11A shows an example of box plots for the WES TML counts versus clinical response.
Figure 11B:
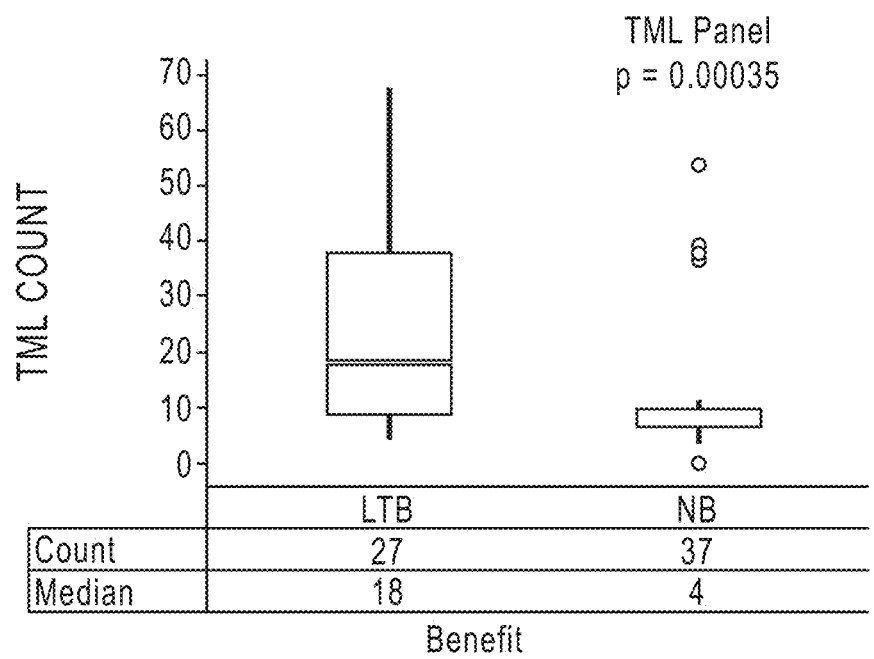
FIG. 11B shows an example of box plots for the somatic mutation counts intersecting with the targeted panel versus clinical response.

Higher somatic mutation counts were associated with clinical response to immune checkpoint blockade inhibitors in studies by Rizvi et al. (2016 Science. 348:124-128) and Snyder et al. (2014 N Eng J Med. 371:2189-2199). FIGS. 10A-10B and 11A-11B show an in silico analysis of the results reported in the Rizvi and Snyder studies using whole exome sequencing (WES). FIGS. 10A and 11A show box plots for the WES TML counts versus clinical response for results by Rizvi and results by Snyder, respectively. To compare with the targeted panel, the somatic mutation counts intersecting with the targeted panel including 409 genes were determined and plotted. FIGS. 10B and 11B show box plots for the somatic mutation counts intersecting with the targeted panel versus clinical response. The results suggest the targeted panel is sufficiently large to predict potential clinical outcome. P-values were determined using the Mann-Whitney Exact test with no assumptions.

Figure 12:
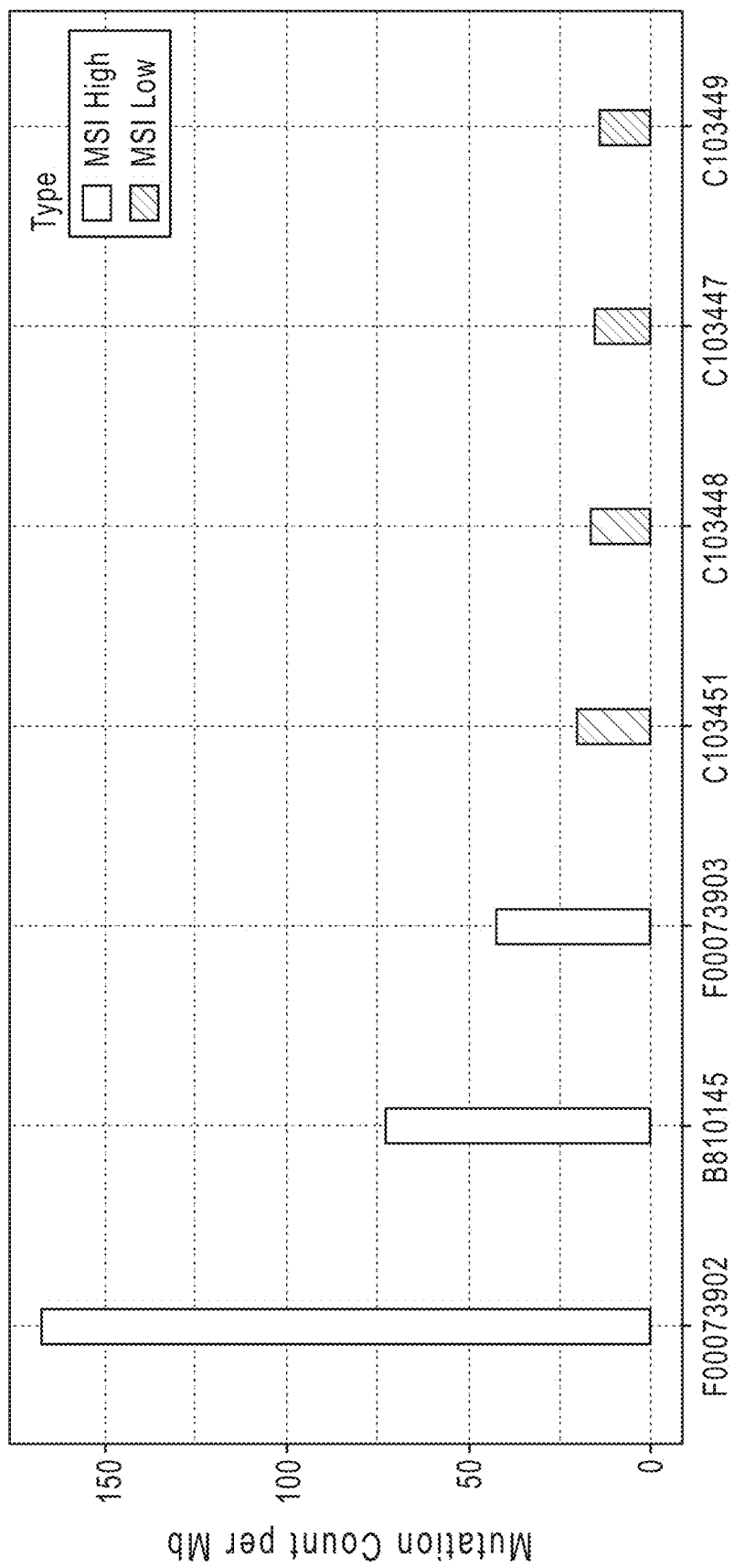
FIG. 12 shows an example of mutation counts per Mb for MSI high and MSI low samples.

High mutation load correlates with microsatellite instability (MSI) in colorectal cancer. Thus MSI status can be used for benchmarking. A batch of 7 colorectal cancer (CRC) tumor samples in which three had known MSI high status and four had known MSI low status were tested using the TML detection method described with respect to FIG. 1. FIG. 12 shows the mutation counts per Mb for MSI high and MSI low samples. MSI high status correlates to high mutation count per Mb in CRC tumor sample. The results show that the TML detection method successfully stratified MSI high and MSI low samples based on mutation counts per Mb.

In some embodiments, sources of DNA damage related to the somatic variants identified by the filtering step 106 may be provided in a report to the user. Sources of DNA damage may include, but are not limited to, ultraviolet (UV) light, tobacco smoke, FFPE deamination and spontaneous deamination of 5-methylcytosine. Table 4 lists the types of somatic mutations consistent with damage from these sources.

TABLE 4

| SOURCE OF DAMAGE | TYPES OF SOMATIC MUTATIONS |
|---|---|
| (1) Spontaneous deamination of 5-methylcytosine | High C > T at CpG |
| (2) UV damage | High C > T at CpC, CpC, TpC, T > A and T > C |
| (3) Smoking damage | High C > A |
| (4) FFPE processing damage | High C > T (site independent) |

The references for the relationships given in Table 4 are (1) Alexandrov L B et al. Nature, 2013; (2) Hayward N K et al. Nature, 2017; (3) Alexandrov L B et al. Cancer Etiology, 2016; and (4) Wong S Q et al. BMC Medical Genomics, 2014.

In some embodiments, the processor may calculate the percentages of the somatic mutations identified by the filtering step 106 that match the types of somatic mutations consistent with the various sources of damage. Table 5 gives an example of percentages calculated for identified somatic variants matching the types of somatic mutations given in Table 4. "Rest" is for those identified somatic variants that did not match any of the types of somatic mutations given in Table 4.

TABLE 5

Figure 13:
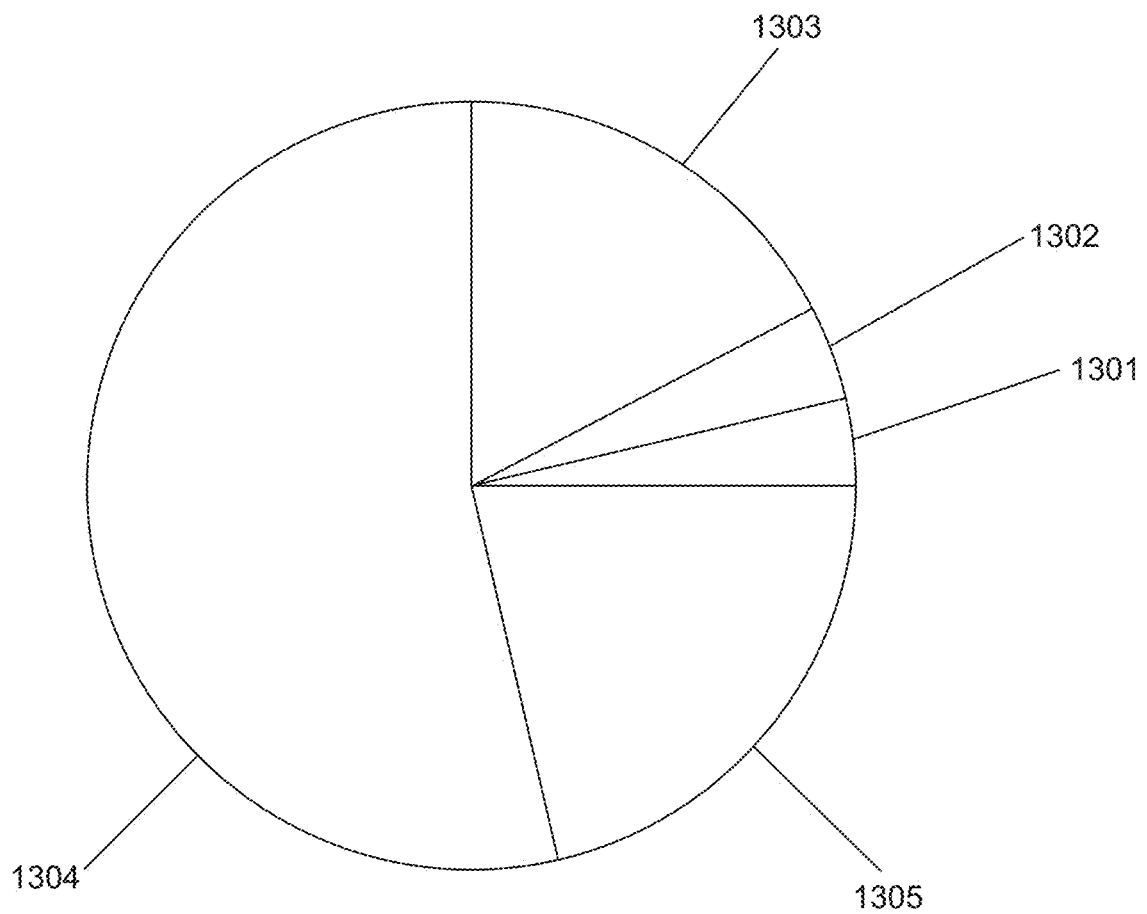
FIG. 13 is a pie chart for the pattern of somatic mutations for the example of percentage values given in Table 4.

| TYPES OF SOMATIC MUTATIONS | PERCENTAGE | FIG. 13 SECTOR |
|---|---|---|
| T > A and T > C | 54.2% | 1304 |
| Rest | 20.8% | 1305 |
| C > A | 16.7% | 1303 |
| C > T at NCC, CC[ACT], TC[ACT] | 4.2% | 1302 |
| C > T at [AG]CG | 4.2% | 1301 |

FIG. 13 is a pie chart for the pattern of somatic mutations for the example of percentage values given in Table 4. The sectors 1301, 1302, 1303, 1304 and 1305 in the pie chart are noted in Table 4. In some embodiments, the pie chart of FIG. 13 and information of Tables 4 and 5 may be included in a report for the user.

In some embodiments, the somatic mutations identified by the filtering step 106 may be further analyzed to produce various graphs, pie charts and histograms for a report. For example, the percentages of identified somatic mutations having certain types of substitutions may be calculated and displayed in a pie chart. Examples of types of substitutions include C>A, C>G, C>T, T>A, T>C and T>G.

The targeted panel and method for estimating tumor mutation load described herein provide improvements to the technology over whole exome sequencing (WES). Sequence assembly methods must be able to assemble and/or map a large number of reads efficiently, such as by minimizing use of computational resources. For example, the sequencing of a human size genome can result in tens or hundreds of millions of reads that need to be assembled before they can be further analyzed. Computer processing of the nucleic acid sequence reads from targeted sequencing reduces computational requirements and memory requirements versus processing for WES data. For WES, 30 Mb of the tumor genome would be covered. The data resulting from the nucleic acid sequence reads of the 30 Mb would require computations to detect variants and storage. In comparison, the targeted panel that covers approximately 1.7 Mb of the tumor genome would require substantially fewer computations for detecting variants and substantially less memory for storage of the nucleic acid sequence reads and variant data.

The targeted panel and method for estimating tumor mutation load for a tumor only sample described herein provide improvements to the technology over matched tumor-normal sample processing. In some cases, a matched normal sample for the tumor sample may not be available. When the matched normal sample is available, detecting variants in the nucleic acid sequence reads from the normal sample require at least the same amount of processing as for the tumor sample, thereby at least doubling the computations and memory requirements.

According to an exemplary embodiment, there is provided a method of analyzing a tumor sample genome for a mutation load, including the following steps: (1) detecting variants in a plurality of nucleic acid sequence reads to produce a plurality of detected variants, wherein the nucleic acid sequence reads correspond to a plurality of targeted locations in the tumor sample genome, wherein the detected variants include somatic variants and germ-line variants; (2) annotating one or more detected variants of the plurality of detected variants with an annotation information from one or more population databases, wherein the population databases include information associated with variants in a population, wherein the annotation information includes a minor allele frequency associated with a given variant; (3) filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants; (4) counting the identified somatic variants to give a number of somatic variants; (5) determining a number of bases in covered regions of the targeted locations in the tumor sample genome; and (6) calculating a number of somatic variants per megabase by dividing the number of identified somatic variants by the number of bases in the covered regions to produce the mutation load for the tumor sample genome. The MAF range may be from 0 to $10^{-6}$. The population databases may include one or more of a 1000 genomes database, a 5000 exomes database and an Exome Aggregation Consortium (ExAC) database. The rule set for the filtering step may further comprise retaining the detected variants that are single nucleotide variants (SNVs). The rule set may further comprise retaining the detected variants that are SNVs, insertion variants and deletion variants (indels). The rule set may further comprise removing the detected variants that are SNVs corresponding to SNPs in the UCSC Common SNP database. The rule set may further comprise removing the detected variants in regions having homopolymer lengths greater than seven. The detecting variants may be configured by variant caller parameters, including a minimum allele frequency parameter, a strand bias parameter and a data quality stringency parameter. The minimum allele frequency parameter may be in a range from 0.001 to 0.15, the strand bias parameter may be in a range from 0.54 to 0.95 and the data quality stringency parameter is in a range from 5 to 25. The method may further comprise associating sources of somatic mutation damage with the identified somatic variants.

According to an exemplary embodiment, there is provided a system for analyzing a tumor sample genome for a mutation load, comprising a processor and a data store communicatively connected with the processor, the processor configured to perform the steps including: detecting variants in a plurality of nucleic acid sequence reads to produce a plurality of detected variants, wherein the nucleic acid sequence reads correspond to a plurality of targeted locations in the tumor sample genome, wherein the detected variants include somatic variants and germ-line variants; annotating one or more detected variants of the plurality of detected variants with an annotation information from one or more population databases stored in the data store, wherein the population databases include information associated with variants in a population, wherein the annotation information includes a minor allele frequency associated with a given variant; filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants; counting the identified somatic variants to give a number of somatic variants; determining a number of bases in covered regions of the targeted locations in the tumor sample genome; and calculating a number of somatic variants per megabase by dividing the number of identified somatic variants by the number of bases in the covered regions to produce the mutation load for the tumor sample genome. The MAF range may be from 0 to $10^{-6}$. The population databases may include one or more of a 1000 genomes database, a 5000 exomes database and an Exome Aggregation Consortium (ExAC) database. The rule set for the filtering step may further comprise retaining the detected variants that are single nucleotide variants (SNVs). The rule set may further comprise retaining the detected variants that are SNVs, insertion variants and deletion variants (indels). The rule set may further comprise removing the detected variants that are SNVs corresponding to SNPs in the UCSC Common SNP database. The rule set may further comprise removing the detected variants in regions having homopolymer lengths greater than seven. The detecting variants may be configured by variant caller parameters, including a minimum allele frequency parameter, a strand bias parameter and a data quality stringency parameter. The minimum allele frequency parameter may be in a range from 0.001 to 0.15, the strand bias parameter may be in a range from 0.54 to 0.95 and the data quality stringency parameter is in a range from 5 to 25. The steps may further comprise associating sources of somatic mutation damage with the identified somatic variants.

According to an exemplary embodiment, there is provided a non-transitory machine-readable storage medium comprising instructions which, when executed by a processor, cause the processor to perform a method for analyzing a tumor sample genome for a mutation load, including: (1) detecting variants in a plurality of nucleic acid sequence reads to produce a plurality of detected variants, wherein the nucleic acid sequence reads correspond to a plurality of targeted locations in the tumor sample genome, wherein the detected variants include somatic variants and germ-line variants; (2) annotating one or more detected variants of the plurality of detected variants with an annotation information from one or more population databases, wherein the population databases include information associated with variants in a population, wherein the annotation information includes a minor allele frequency associated with a given variant; (3) filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants; (4) counting the identified somatic variants to give a number of somatic variants; (5) determining a number of bases in covered regions of the targeted locations in the tumor sample genome; and (6) calculating a number of somatic variants per megabase by dividing the number of identified somatic variants by the number of bases in the covered regions to produce the mutation load for the tumor sample genome. The MAF range may be from 0 to $10^{-6}$. The population databases may include one or more of a 1000 genomes database, a 5000 exomes database and an Exome Aggregation Consortium (ExAC) database. The rule set for the filtering step may further comprise retaining the detected variants that are single nucleotide variants (SNVs). The rule set may further comprise retaining the detected variants that are SNVs, insertion variants and deletion variants (indels). The rule set may further comprise removing the detected variants that are SNVs corresponding to SNPs in the UCSC Common SNP database. The rule set may further comprise removing the detected variants in regions having homopolymer lengths greater than seven. The detecting variants may be configured by variant caller parameters, including a minimum allele frequency parameter, a strand bias parameter and a data quality stringency parameter. The minimum allele frequency parameter may be in a range from 0.001 to 0.15, the strand bias parameter may be in a range from 0.54 to 0.95 and the data quality stringency parameter is in a range from 5 to 25. The steps may further comprise associating sources of somatic mutation damage with the identified somatic variants.

In various embodiments, nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, fluorescent-based detection systems, single molecule methods, etc.

Figure 14:
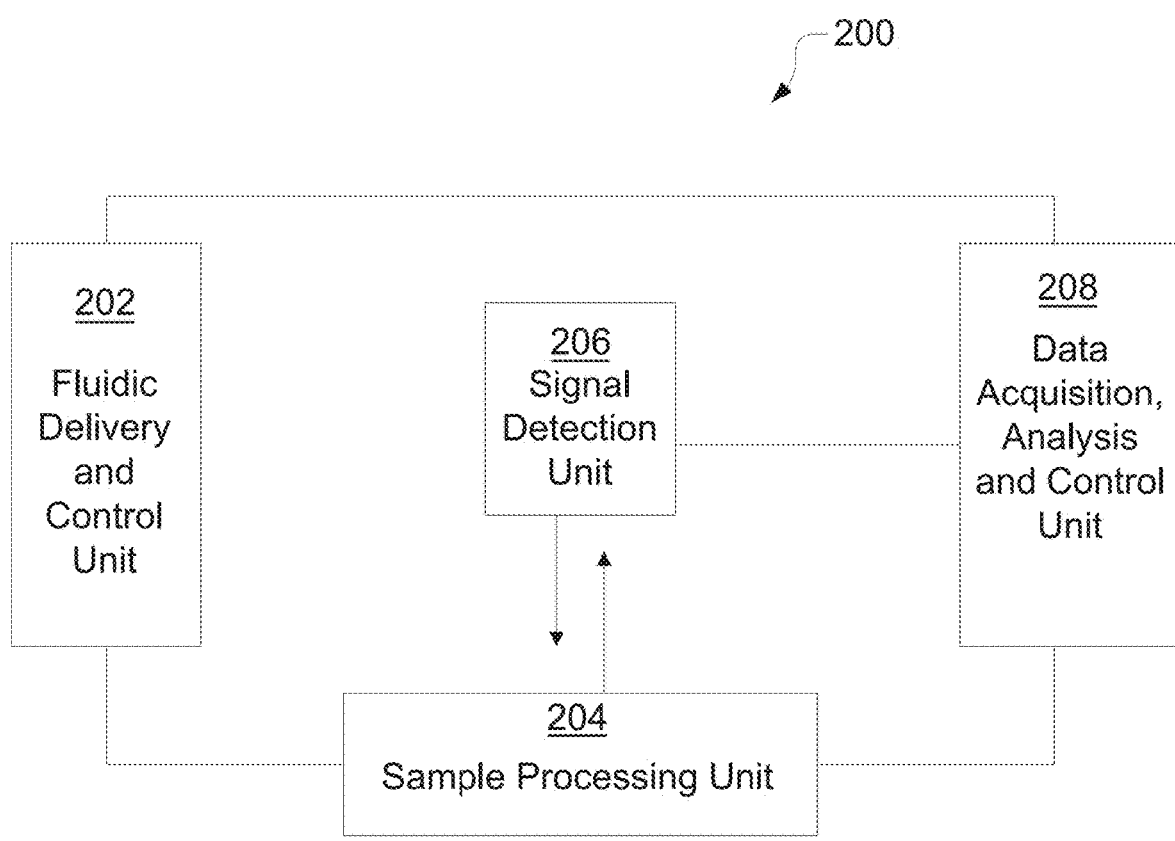
FIG. 14 is a schematic diagram of an exemplary system for reconstructing a nucleic acid sequence, in accordance with various embodiments.

Various embodiments of nucleic acid sequencing platforms, such as a nucleic acid sequencer, can include components as displayed in the block diagram of FIG. 14. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion sensor, such as an ion sensitive layer overlying a CMOS, a current detector, or the like. The signal detection unit 206 can include an excitation system to cause a probe, such as a fluorescent dye, to emit a signal. The expectation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

FIG. 15 is a schematic diagram of a system for annotating genomic variants, in accordance with various embodiments.

As depicted herein, annotation system 300 can include a nucleic acid sequence analysis device 304 (for example, nucleic acid sequencer, real-time/digital/quantitative PCR instrument, microarray scanner, etc.), an analytics computing server/node/device 302, a display 338 and/or a client device terminal 336, and one or more public 330 and proprietary 332 annotations content sources.

In various embodiments, the analytics computing server/node/device 302 can be communicatively connected to the nucleic acid sequence analysis device 304, client device terminal 336, public annotations content source 330 and/or proprietary annotations content source 332 via a network connection 334 that can be either a "hardwired" physical network connection (for example, Internet, LAN, WAN, VPN, etc.) or a wireless network connection (for example, Wi-Fi, WLAN, etc.).

In various embodiments, the analytics computing device/server/node 302 can be a workstation, mainframe computer, distributed computing node (part of a "cloud computing" or distributed networking system), personal computer, mobile device, etc. In various embodiments, the nucleic acid sequence analysis device 304 can be a nucleic acid sequencer, real-time/digital/quantitative PCR instrument, microarray scanner, etc. It should be understood, however, that the nucleic acid sequence analysis device 304 can essentially be any type of instrument that can generate nucleic acid sequence data from samples obtained from an individual 306.

The analytics computing server/node/device 302 can be configured to host a mapping engine 308, a variant calling engine 310, a decision support module 312 and a reporter module 316.

The mapping engine 308 can be configured to align or map a query nucleic acid sequence read to a reference sequence. Generally, the length of the sequence read is substantially less than the length of the reference sequence. In reference sequence mapping/alignment, sequence reads can be assembled against an existing backbone sequence (for example, reference sequence, etc.) to build a sequence that is similar but not necessarily identical to the backbone sequence. Once a backbone sequence is found for an organism, comparative sequencing or re-sequencing can be used to characterize the genetic diversity within the organism's species or between closely related species. In various embodiments, the reference sequence can be a whole/partial genome, whole/partial exome, whole/partial transcriptome, etc.

In various embodiments, the sequence read and reference sequence can be represented as a sequence of nucleotide base symbols in base space. In various embodiments, the sequence read and reference sequence can be represented as one or more color symbols in color space. In various embodiments, the sequence read and reference sequence can be represented as nucleotide base symbols with signal or numerical quantitation components in flow space.

In various embodiments, the alignment of the sequence read and reference sequence can include a limited number of mismatches between the bases that comprise the sequence read and the bases that comprise the reference sequence. Generally, at least a portion of the sequence read can be aligned to a portion of the reference sequence, such as a reference nuclear genome, a reference mitochondrial genome, a reference prokaryotic genome, a reference chloroplast genome, or the like, in order to minimize the number of mismatches between the sequence fragment and the reference sequence.

The variant calling engine 310 can be configured to receive aligned sequence reads from the mapping engine 308 and analyze the aligned sequence reads to detect and call or identify one or more variants within the reads. Examples of variants that can be called by a variant calling engine 310 include but are not limited to: single nucleotide variants (SNV), single nucleotide polymorphisms (SNP), nucleotide insertions or deletions (indels), copy number variations (CNV) identification, inversion polymorphisms, and the like.

The reporter module 316 can be in communications with the decision support module 312 and be configured to generate a summary report of the called genomic variants that have been annotated by the annotator component 314 that can be part of the decision support module 312.

The decision support module can include an annotator component 314, a variome data store 322, an annotations data store 324, a filtering component 328 and/or an annotations importer component 326. In various embodiments, the annotator component 314 can be in communication with the variant calling engine 310, the variome data store 322 and/or the annotations data store 324. That is, the annotator component 314 can request and receive data and information (through, for example, data streams, data files, text files, etc.) from variant calling engine 310, variome data store 322 and annotations data store 324. In various embodiments, the variant calling engine 310 can be configured to communicate variants called for a sample genome in various formats, such as, but not limited to, variant call format (VCF), generic feature format (GFF) heirachical data format (HDF), genome variation format (GVF), or HL7 formatted data. It should be understood, however, that the called variants can be communicated using any file format where the called variant information can be parsed and/or extracted for later processing/analysis.

The variome data store 322 can be configured to store the variant calls received from the variant calling engine 310 and/or the annotator component 314 in a format that is accessible for mining.

That is, the called variant data can be maintained as a database or instantiated in some other persistent (and queryable) electronic form in the device memory (for example, hard drive, RAM, ROM, etc.) of the analytics computing server/node/device 302. The called variant data can be structured and use a common syntax and semantic model throughout or include appropriate interpreters between formats that allow for one-to-one mapping between terms and data types. In various embodiments, the variome data store 322 can be an indexed database table of variants. In particular embodiments, the indexed database can be configured for fast querying and filtering operations.

The annotations data store 324 can be in communications with the annotations importer component 326 and be configured to store data and information that can be used by the annotator component 314 to annotate the called variants. That is, the annotations data store 324 can store annotation data and information that can be relevant to the role that the called variant plays in the function, such as at a chromosome level, gene level, a transcript level, a protein level, or the like, (for example, functional type annotations) and/or the biological impact (for example, interpretive type annotations) of the called variants. In various embodiments, functional type annotations can include, but are not limited to: locus classification of the called variant, protein function impact score of the called variant, amino acid changes resulting from the called variant, gene/transcripts affected by the called variant, etc. In various embodiments, interpretive type annotations can include, but are not limited to: disease states or susceptibility to a disease (for example, cancer, diabetes, hypertension, heart disease, etc.) associated with the called variant, impacts that the called variant has on a particular therapeutic regimen (for example, drugs, surgical options, medical device, psychiatric therapy, lifestyle changes, drug sensitivities, etc.), presence of the variant on a list of annotated variants, etc. For example, a SNP variant call can be annotated with functional type annotations that point to the transcripts that the called SNP impacts and interpretive type annotations that are directed to diagnosing a particular disease state or a susceptibility to a disease.

The annotations importer component 326 can be configured to receive annotations content from one or more public 330 or proprietary 332 annotations content sources and convert the annotations content into a format that can be stored in the annotations data store 324 and is accessible for mining. That is, the annotations importer component 326 can convert annotations data and/or information into a format that can be stored onto a database or instantiated in some other persistent (and queryable) electronic form in the device memory (for example, hard drive, RAM, ROM, etc.) of the analytics computing server/node/device 302.

In various embodiments, annotations content can be manually entered or uploaded by a user to the annotations importer component 326 via a computer readable storage medium that is communicatively connected (for example, via a serial data bus connection, parallel data bus connection, internet/intranet network connection, etc.) to the analytics computing server/node/device 302. That is, a user can selectively upload annotations content to the annotations data store 324 depending on the requirements of the particular application. Examples of computer readable medium include, but are not limited to: hard drives, network attached storage (NAS), read-only memory, random-access memory, CD-ROMs, CD-Rs, CD-RWs, magnetic tapes, FLASH memory and other optical/non-optical data storage devices.

In various embodiments, annotations content can be automatically requested and sent from public 330 and/or proprietary 332 annotations content sources to the annotations importer component 326 through the use of a data refresh executable or script. That is, the annotations content in the annotations data store 324 can be continuously refreshed as the public 330 and/or proprietary 332 annotations content sources are updated with new or modified annotations content.

In various embodiments, the annotator component 314 can include a functional annotations engine 318 and interpretive annotations engine 320.

The functional annotations engine 318 can be configured to receive called variants from the variome data store 322, associate one or more functional type annotations (stored in the annotations data store 324) to the called variants and update the called variant records in the variome data store 322 with the associated functional type annotations. In various embodiments, the functional annotations engine 318 can be configured to annotate all called variants that fall within a block of overlapping transcripts (in the sample genome) at the same time. That is, the functional annotations engine 318 can group overlapping transcripts together into a "gene block" and then annotate all variants in the gene block together. The advantage here is that all called variants that are potentially mutually interacting can be grouped and annotated together to give researchers/clinicians greater insight into the synergistic or antagonistic interplay between variants.

In various embodiments, the functional annotations engine 318 can be selectively configured to annotate only called variants that fall within a coding region (for example, exons, codons) of the sample genome being annotated. In various embodiments, the functional annotations engine 318 can be selectively configured to annotate only called variants that fall within an intragenic region, such as an intron, of the sample genome being annotated. In various embodiments, the functional annotations engine 318 can be selectively configured to annotate only the called variants in the intergenic region of the sample genome being annotated.

In various embodiments, the functional annotations engine 318 can receive the called variants in the form of a called variant data file (for example, *.vcf or other file format), associate the functional type annotations, and store the variants and annotations to the variome data store 322. In various embodiments, the functional annotations engine 318 can receive the called variants as variant data (for example, variant base identity and genome position, etc.), associates one or more functional type annotations to the called variant and directly updates the called variant record in the variome data store 322 with the associated functional type annotations information. That is, the functional annotations engine 318 can receive called variants directly from the variome data store 322, annotate them and save them back on the variome data store 322 or alternate data store.

The interpretive annotations engine 320 can be configured to receive called variants from the variome data store 322, associate one or more interpretive type annotations (stored in the annotations data store 324) to the called variants and update the called variant records in the variome data store 322 with the associated interpretive type annotations.

In various embodiments, the interpretive annotations engine 320 receives the called variants in the form of a called variant data file (for example, *.vcf or other file format), associate the interpretive type annotations, and store the variants and annotations to the variome data store 322. In various embodiments, the interpretive annotations engine 318 receives the called variants as variant data (for example, variant base identity and genome position, etc.), associates one or more interpretive type annotations to the called variant and directly updates the called variant record in the variome data store 322 with the associated interpretive type annotations information.

In various embodiments, the system can be configured to automate the processing of sample data. For example, a workflow can be selected to define how the data is processed by the mapping engine 308, the variant calling engine 310, and the annotator component 314. In particular embodiments, a workflow can be selected when setting up the run on the nucleic acid sequence analysis device 304 and the data can be automatically uploaded to the analytics computing device 302. Additionally, the workflow can be automatically launched when the data has been uploaded. In other embodiments, the data can be uploaded, manually or automatically, from the nucleic acid sequence analysis device 304 and the workflow can be selected and launched manually. Generally, once the workflow has been selected and launched, analysis can proceed from through the mapping engine 308, the variant calling engine, 310, and the annotator component 314 without further intervention by a user.

The filtering component 328 can be configured to allow a user to set filter conditions to filter the called variants that are included in the summary report generated by the reporter module 316. Examples of filter conditions include, but are not limited to, filtering for: variants that are non-synonymous and fall within a particular gene, variants that are associated with a particular disease condition, variants that have a functional score of greater or less than a selected value, novel variants that are not present in a functional type annotations source, variants that fall in gene panel regions (defined by user), etc. In various embodiments, the filtering component 328 can utilize combinations of filters, such as for example filtering for variants that fall within a particular gene and have a functional score indicative of a significant effect.

In various embodiments, the filtering component 328 can be configured with a collection of filters to select for variants with a high likelihood of having possible functional significance. For example, the filtering component 328 can select for missense mutations and nonsense mutations and exclude synonymous mutations. Still further, the filtering component 328 can select for variants that affect allele frequency. Also, the filtering component 328 may select or exclude variants at positions of known significance, such as positions known to have a high incidence of mutation in cancers, positions with a low or high number of false positive variant calls, positions known to have a minimal functional impact, or the like.

In various embodiments, the variome data 322 and the annotations data 324 stores can be combined into a single data store configured to store both called variant data and variant annotations information.

Client terminal 336 can be a thin client or thick client computing device. In various embodiments, client terminal 336 can have a web browser (for example, INTERNET EXPLORER™ FIREFOX™, SAFARI™, etc.) that can be used to communicate information to and/or control the operation of the mapping engine 308, variant calling engine 310, decision support module 312, annotator component 314, filtering component 328, annotations importer component 326, variome data store 322, annotations data store 324, functional annotations engine 318 and/or interpretive annotations engine 320 using a browser to control their function. For example, the client terminal 336 can be used to configure the operating parameters (for example, match scoring parameters, annotations parameters, filtering parameters, data security and retention parameters, etc.) of the various modules, depending on the requirements of the particular application. Similarly, client terminal 336 can also be configured to display the results of the analysis performed by the decision support module 312 and the nucleic acid sequencer 304.

It should be understood that the various data stores disclosed as part of system 300 can represent hardware-based storage devices (for example, hard drive, flash memory, RAM, ROM, network attached storage, etc.) or instantiations of a database stored on a standalone or networked computing device(s).

It should also be appreciated that the various data stores and modules/engines shown as being part of the system 300 can be combined or collapsed into a single module/engine/data store, depending on the requirements of the particular application or system architecture. Moreover, in various embodiments, the system 300 can comprise additional modules, engines, components or data stores as needed by the particular application or system architecture or to extend functionality.

In various embodiments, the system 300 can be configured to process the nucleic acid reads in color space. In various embodiments, system 300 can be configured to process the nucleic acid reads in base space. In various embodiments, system 300 can be configured to process the nucleic acid sequence reads in flow space. It should be understood, however, that the system 300 disclosed herein can process or analyze nucleic acid sequence data in any schema or format as long as the schema or format can convey the base identity and position (or position range) of the nucleic acid sequence within the reference sequence.

In various embodiments, the system 300 can be configured to distinguish between positions with a called variant, positions that have been called as reference, and positions with no call. Positions with a called variant can include positions where sufficient evidence was provided by the reads to indicate the specimen sequence contains a variant. Positions that have been called as reference can include positions where there is sufficient evidence to support the conclusion that the specimen sequence is substantially identical to the reference sequence at the position. Positions with no call can include positions where there is insufficient evidence to determine if the specimen sequence is the same as or different from the reference sequence. For example, positions with no call can include positions with low coverage, positions with low base quality, or positions where the read sequences indicate different bases with insufficient homogeneity to determine the sequence with sufficient confidence. Generally, positions with no call can be indicated as matching the reference sequence and may be excluded from reporting of variants.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of analyzing a tumor sample genome for a mutation load, comprising:
   selectively amplifying nucleic acid sequences at targeted locations in the tumor sample genome by a targeted panel with a low sample input from the tumor sample to generate a plurality of nucleic acid sequence reads;
   detecting variants in the plurality of nucleic acid sequence reads to produce a plurality of detected variants, wherein the detected variants include somatic variants and germ-line variants;
   annotating one or more detected variants of the plurality of detected variants with an annotation information from one or more population databases, wherein the population databases include information associated with variants in a population, wherein the annotation information includes a minor allele frequency associated with a given variant;
   filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants;
   counting the identified somatic variants to give a number of somatic variants;
   determining a number of bases in covered regions of the targeted locations in the tumor sample genome; and
   calculating a number of somatic variants per megabase by dividing the number of somatic variants by the number of bases in the covered regions to produce the mutation load for the tumor sample genome.

2. The method of claim 1, wherein the MAF range is from 0 to $10^{-6}$.

3. The method of claim 1, wherein the population databases include one or more of a 1000 genomes database, a 5000 exomes database and an Exome Aggregation Consortium (ExAC) database.

4. The method of claim 1, wherein the rule set further comprises retaining the detected variants that are single nucleotide variants (SNVs).

5. The method of claim 1, wherein the rule set further comprises retaining the detected variants that are SNVs, insertion variants and deletion variants (indels).

6. The method of claim 1, wherein the rule set further comprises removing the detected variants that are SNVs corresponding to SNPs in a UCSC Common SNP database.

7. The method of claim 1, wherein the rule set further comprises removing the detected variants in regions having homopolymer lengths greater than seven.

8. The method of claim 1, wherein the detecting variants is configured by variant caller parameters, the variant caller parameters including a minimum allele frequency parameter, a strand bias parameter and a data quality stringency parameter.

9. The method of claim 8, wherein the minimum allele frequency parameter is in a range from 0.001 to 0.15, the strand bias parameter is in a range from 0.54 to 0.95 and the data quality stringency parameter is in a range from 5 to 25.

10. The method of claim 1, further comprising associating sources of somatic mutation damage with the identified somatic variants.

11. A system for analyzing a tumor sample genome for a mutation load, comprising a processor and a data store communicatively connected with the processor, the processor configured to execute instructions, which, when executed by the processor, cause the system to perform a method, including:
   selectively amplifying nucleic acid sequences at targeted locations in the tumor sample genome by a targeted panel with a low sample input from the tumor sample to generate a plurality of nucleic acid sequence reads;
   detecting variants in the plurality of nucleic acid sequence reads to produce a plurality of detected variants, wherein the detected variants include somatic variants and germ-line variants;
   annotating one or more detected variants of the plurality of detected variants with an annotation information from one or more population databases stored in the data store, wherein the population databases include information associated with variants in a population, wherein the annotation information includes a minor allele frequency associated with a given variant;
   filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants;

counting the identified somatic variants to give a number of somatic variants; determining a number of bases in covered regions of the targeted locations in the tumor sample genome; and calculating a number of somatic variants per megabase by dividing the number of somatic variants by the number of bases in the covered regions to produce the mutation load for the tumor sample genome.

12. The system of claim 11, wherein the MAF range is from 0 to $10^{-6}$.

13. The system of claim 11, wherein the population databases include one or more of a 1000 genomes database, a 5000 exomes database and an Exome Aggregation Consortium (ExAC) database.

14. The system of claim 11, wherein the rule set further comprises retaining the detected variants that are single nucleotide variants (SNVs).

15. The system of claim 11, wherein the rule set further comprises removing the detected variants that are SNVs corresponding to SNPs in a UCSC Common SNP database.

16. The system of claim 11, wherein the rule set further comprises removing the detected variants in regions having homopolymer lengths greater than seven.

17. The system of claim 11, wherein the detecting variants is configured by variant caller parameters, the variant caller parameters including a minimum allele frequency parameter, a strand bias parameter and a data quality stringency parameter.

18. The system of claim 17, wherein the minimum allele frequency parameter is in a range from 0.001 to 0.15, the strand bias parameter is in a range from 0.54 to 0.95 and the data quality stringency parameter is in a range from 5 to 25.

19. The system of claim 11, further comprising associating sources of somatic mutation damage with the identified somatic variants.

20. A non-transitory machine-readable storage medium comprising instructions which, when executed by a processor, cause the processor to perform a method of analyzing a tumor sample genome for a mutation load, comprising:

selectively amplifying nucleic acid sequences at targeted locations in the tumor sample genome by a targeted panel with a low sample input from the tumor sample to generate a plurality of nucleic acid sequence reads;

detecting variants in the plurality of nucleic acid sequence reads to produce a plurality of detected variants, wherein the detected variants include somatic variants and germ-line variants;

annotating one or more detected variants of the plurality of detected variants with an annotation information from one or more population databases, wherein the population databases include information associated with variants in a population, wherein the annotation information includes a minor allele frequency associated with a given variant;

filtering the plurality of detected variants, wherein the filtering applies a rule set to the detected variants to retain the somatic variants, the rule set including retaining the detected variants whose minor allele frequency (MAF) is within a MAF range, wherein the filtering produces identified somatic variants;

counting the identified somatic variants to give a number of somatic variants;

determining a number of bases in covered regions of the targeted locations in the tumor sample genome; and calculating a number of somatic variants per megabase by dividing the number of identified somatic variants by the number of bases in the covered regions to produce the mutation load for the tumor sample genome.

* * * * *

UNITED STATES PATENT AND TRADEMARK OFFICE
CERTIFICATE OF CORRECTION

PATENT NO. : 11,101,019 B2
APPLICATION NO. : 15/834520
DATED : August 24, 2021
INVENTOR(S) : Ruchi Chaudhary Page 1 of 2

It is certified that error appears in the above-identified patent and that said Letters Patent is hereby corrected as shown below:

On the Title Page

Delete the title page and replace with the attached title page showing the corrected number of claims.

In the Claims

In Column 26, Lines 4-36, delete Claim 20.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

(12) United States Patent
Chaudhary et al.

(10) Patent No.: US 11,101,019 B2
(45) Date of Patent: Aug. 24, 2021

(54) METHODS FOR DETECTING MUTATION LOAD FROM A TUMOR SAMPLE

(71) Applicant: LIFE TECHNOLOGIES CORPORATION, Carlsbad, CA (US)

(72) Inventors: Ruchi Chaudhary, Redwood City, CA (US); Fiona Hyland, San Mateo, CA (US)

(73) Assignee: Life Technologies Corporation, Carlsbad, CA (US)

(*) Notice: Subject to any disclaimer, the term of this patent is extended or adjusted under 35 U.S.C. 154(b) by 899 days.

(21) Appl. No.: 15/834,520

(22) Filed: Dec. 7, 2017

(65) Prior Publication Data

US 2018/0165410 A1 Jun. 14, 2018

Related U.S. Application Data

(60) Provisional application No. 62/431,493, filed on Dec. 8, 2016, provisional application No. 62/579,645, filed on Oct. 31, 2017, provisional application No. 62/585,598, filed on Nov. 14, 2017.

(51) Int. Cl.
*G16B 20/00* (2019.01)
*G16B 30/00* (2019.01)

(52) U.S. Cl.
CPC ............. *G16B 20/00* (2019.02); *G16B 30/00* (2019.02)

(58) Field of Classification Search
CPC .................................. G16B 20/00; G16B 30/00
USPC ............................................................. 702/19
See application file for complete search history.

(56) References Cited

U.S. PATENT DOCUMENTS

2014/0336996 A1 11/2014 Sun et al.
2017/0213008 A1 7/2017 Venn

FOREIGN PATENT DOCUMENTS

WO WO-2018106884 A1 6/2018

OTHER PUBLICATIONS

Alexandrov LB et al., "Mutational Signatures Associated with Tobacco Smoking In Human Cancer", Science, 2016, vol. 354, No. 6312, pp. 618-622.
Alexandrov LB et al., "Signatures of Mutational Processes in Human Cancer", Nature, 2013, vol. 500, pp. 415-421.
Hayward NK et al., "Whole-Genome Landscapes of Major Melanoma Subtypes", Nature, 2017, vol. 545, pp. 175-180.
PCT/US2019/048085, Search Report and Written Opinion, dated Dec. 2, 2019.
Rizvi et al., "Mutational landscape determines sensitivity to PD-1 blockade in non-small cell lung cancer", Science, 2016, vol. 348, pp. 124-128.
Snyder et al., "Genetic Basis for Clinical Response to CTLA-4 Blockade in Melanoma", N Engl J Med, 2014, vol. 371, pp. 2189-2199.
Van Allen et al., "Genomic correlates of response to CTLA-4 blockade in metastatic melanoma", Science, 2015, vol. 350, No. 6257, pp. 207-211.
Wong SQ et al., "Sequence Artefacts in A Prospective Series of Formalin-Fixed Tumours Tested for Mutations in Hotspot Regions by Massively Parallel Sequencing", BMC Medical Genomics, 2014, vol. 7, Article No. 23, 10 pages.
Campesato, L. et al., "Comprehensive cancer-gene panels can be used to estimate mutational load and predict clinical benefit to PD-1 blockade in clinical practice", *Oncotarget*, vol. 6, No. 33, Oct. 1, 2015, 34221-34227.
PCT/US2017/065053, International Search Report and Written Opinion dated Mar. 22, 2018, 14 pp.
Roszik, J. et al., "Novel algorithmic approach predicts tumor mutation load and correlates with immunotherapy clinical outcomes using a defined gene mutation set", *BMC Medicine*, vol. 14, No. 1; DOI: 10.1186/s12916-016-0705-4, Oct. 25, 2016, 8 pp.
Spranger, S. et al., "Density of immunogenic antigens does not explain the presence or absence of the T-cell-inflamed tumor microenvironment in melanoma", *Proceedings National Academy of Sciences (PNAS)*, vol. 113, No. 48; DOI: 10.1073/pnas. 1609376113, Nov. 11, 2016, E7759-E7768.

*Primary Examiner* — Jerry Lin
(74) *Attorney, Agent, or Firm* — Carolyn Koenig

(57) ABSTRACT

A targeted panel with low sample input requirements from a tumor only sample may be processed to estimate mutation load in a tumor sample. The method may include: detecting variants in nucleic acid sequence reads corresponding to targeted locations in the tumor sample genome; annotating detected variants with an annotation information from a population database; filtering the detected variants, wherein the filtering rule set retains the somatic variants and removes germ-line variants; counting the identified somatic variants to give a number of somatic variants; determining a number of bases in covered regions of the targeted locations in the tumor sample genome; and calculating a number of somatic variants per megabase, provides an estimate of the mutation load per megabase in the tumor sample genome.

19 Claims, 15 Drawing Sheets